(12) United States Patent
Hashimoto et al.

(10) Patent No.: US 11,744,519 B2
(45) Date of Patent: Sep. 5, 2023

(54) BIOLOGICAL INFORMATION MEASUREMENT DEVICE

(71) Applicant: SEIKO EPSON CORPORATION, Tokyo (JP)

(72) Inventors: Taki Hashimoto, Shiojiri (JP); Hiromitsu Mizukami, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 982 days.

(21) Appl. No.: 16/526,217

(22) Filed: Jul. 30, 2019

(65) Prior Publication Data

US 2020/0037960 A1 Feb. 6, 2020

(30) Foreign Application Priority Data

Jul. 31, 2018 (JP) ................. 2018-143350

(51) Int. Cl.
*A61B 5/1455* (2006.01)
*A61B 5/00* (2006.01)
*A61B 5/024* (2006.01)

(52) U.S. Cl.
CPC ........ *A61B 5/7203* (2013.01); *A61B 5/02427* (2013.01); *A61B 5/7207* (2013.01); *A61B 5/7214* (2013.01); *A61B 5/681* (2013.01)

(58) Field of Classification Search
CPC . A61B 5/1455; A61B 5/7203; A61B 5/02427; A61B 5/7207; A61B 5/7214
See application file for complete search history.

(56) References Cited

U.S. PATENT DOCUMENTS

| | | |
|---|---|---|
| 2009/0156948 A1 | 6/2009 | Shimizu et al. |
| 2016/0081567 A1 | 3/2016 | Nousiainen et al. |
| 2016/0120477 A1 | 5/2016 | Takahashi |
| 2017/0027459 A1 | 2/2017 | Shimuta |
| 2017/0164848 A1 | 6/2017 | Nadeau et al. |
| 2017/0251963 A1 | 9/2017 | Hashimoto et al. |
| 2017/0281027 A1 | 10/2017 | Altmejd et al. |

FOREIGN PATENT DOCUMENTS

| | | |
|---|---|---|
| CN | 105982654 A | 10/2016 |
| JP | H07-308299 A | 11/1995 |
| JP | 2013-116210 A | 6/2013 |
| JP | 2015-016188 A | 1/2015 |
| JP | 2016-036728 A | 3/2016 |
| JP | 2016-083007 A | 5/2016 |
| JP | 2016-521190 A | 7/2016 |
| JP | 2016-152965 A | 8/2016 |
| JP | 2017-148584 A | 8/2017 |
| JP | 2017-153876 A | 9/2017 |
| JP | 2017-169690 A | 9/2017 |
| WO | 2007/037100 A1 | 4/2007 |
| WO | 2014/184447 A1 | 11/2014 |
| WO | 2015/159692 A1 | 10/2015 |

*Primary Examiner* — Marjan Fardanesh
(74) *Attorney, Agent, or Firm* — Oliff PLC

(57) ABSTRACT

A biological information measurement device includes a first light emitting portion that emits first light, a second light emitting portion that emits second light, a light receiving portion that receives the first light reflected by an epidermis of a skin, a dermis of the skin, and a subcutaneous layer, and the second light reflected by the epidermis and dermis of the skin, and a processing unit that calculates biological information by removing noise, from a first detection signal output based on the first light received by the light receiving portion, using a second detection signal output based on the second light received by the light receiving portion.

20 Claims, 18 Drawing Sheets

*FIG. 7*

| L (mm) | 0.3 | 0.4 | 0.5 | 0.6 | 0.7 | 0.8 | 0.9 | 1.0 | 1.1 | 1.2 | 1.3 | 1.4 | 1.5 | 1.6 | 1.7 | 1.8 | 1.9 | 2.0 | 2.1 |
|---|---|---|---|---|---|---|---|---|---|---|---|---|---|---|---|---|---|---|---|
| SIGNAL QUALITY | A | B | A | A | A | A | A | A | A | A | A | A | A | B | B | B | B | C | D |
| REALIZABILITY | d | c | b | b | b | a | a | a | a | a | a | a | a | a | a | a | a | a | a |

BIOLOGICAL INFORMATION MEASUREMENT DEVICE

The present application is based on, and claims priority from JP Application Serial Number 2018-143350, filed Jul. 31, 2018, the disclosure of which is hereby incorporated by reference herein in its entirety.

BACKGROUND

1. Technical Field

The present disclosure relates to a biological information measurement device.

2. Related Art

In the related art, a biological information processing device that is worn on a wrist of a subject and measures a pulse wave of the subject is known (see, for example, JP-A-2015-16188).

The biological information processing device described in JP-A-2015-16188 includes a pulse wave sensor that detects a pulse wave of a subject, an acceleration sensor that detects a body motion of the subject, a body motion noise removal unit, and a pulse rate calculation unit. The pulse wave sensor includes a light emitting element and a light receiving element.

When a living body is irradiated with light, reflected light intensity fluctuates to reflect changes in blood volume due to light absorption action of hemoglobin in blood. For that reason, the pulse wave sensor outputs a signal indicating a change in blood flow of a subcutaneous tissue as a biological signal by irradiating the subject's wrist with light by the light emitting element and receiving reflected light by the light receiving element.

The acceleration sensor detects triaxial acceleration acting on the biological information processing device, and outputs a signal indicating the detected acceleration as a body motion signal.

The body motion noise removal unit is a filter circuit that separates a pulse wave component and a body motion noise component contained in the biological signal with the biological signal output from the pulse wave sensor and the body motion signal output from the acceleration sensor as input. The filter circuit calculates an estimated body motion noise component from the body motion signal using an adaptive filter and attenuates the estimated body motion noise component from the biological signal to output an estimated pulse wave component as an output signal. The pulse rate calculation unit calculates a pulse rate from the estimated pulse wave component output by the body motion noise removal unit.

With this configuration, it is possible to suppress that the noise component caused by the body motion remains in the estimated pulse wave component extracted and thus, it is possible to calculate the pulse rate even under a situation where the body motion noise is large such as during exercise.

In order to detect biological information with high accuracy, it is necessary to reduce as much as possible the noise component contained in the biological signal from the pulse wave sensor. In the method of JP-A-2015-16188, although an acceleration sensor is used to suppress the body motion noise, this may not be sufficient.

SUMMARY

A biological information measurement device according to a first aspect of the present disclosure includes a first light emitting portion that emits first light, a second light emitting portion that emits second light, a light receiving portion that receives the first light reflected by an epidermis of a skin, a dermis of the skin, and a subcutaneous layer, and the second light reflected by the epidermis and dermis of the skin, and a processing unit that calculates biological information by removing noise from a first detection signal output based on the first light received by the light receiving portion, using a second detection signal output based on the second light received by the light receiving portion.

In the biological information measurement device according to the first aspect, the first light emitting portion and the second light emitting portion may be disposed at positions where a path of the second light in a body of a user is included in a path of the first light in the body of the user.

In the biological information measurement device according to the first aspect, a wavelength of the first light may be 500 nm or more and less than 600 nm, and a wavelength of the second light may be 600 nm or more.

In the biological information measurement device according to the first aspect, a distance between the second light emitting portion and the light receiving portion may be less than 2.0 mm.

A biological information measurement device according to a second aspect of the present disclosure includes a first light emitting portion that emits first light, a second light emitting portion that emits second light, a light receiving portion that receives light from the first light emitting portion and the second light emitting portion and outputs a first detection signal and a second detection signal, and a processing unit that determines biological information based on the first detection signal and the second detection signal, and in which a distance between the second light emitting portion and the light receiving portion is less than 2.0 mm.

In the biological information measurement device according to the second aspect, the distance between the second light emitting portion and the light receiving portion may be a distance between a light emission center of the second light emitting portion and a light reception center of the light receiving portion.

In the biological information measurement device according to the second aspect, the light emission center of the second light emitting portion may be a center of the second light emitting portion in a plan view, and the light reception center of the light receiving portion may be a center of a light receiving surface of the light receiving portion in a plan view.

In the biological information measurement device according to the second aspect, a wavelength of the first light may be 500 nm or more and less than 600 nm, and a wavelength of the second light may be 600 nm or more.

In the biological information measurement device according to the second aspect, a distance between the first light emitting portion and the light receiving portion in a direction from the first light emitting portion toward the light receiving portion may be equal to or greater than a distance between the second light emitting portion and the light receiving portion in a direction from the second light emitting portion toward the light receiving portion.

In the biological information measurement device according to the second aspect, a distance between the second light emitting portion and the light receiving portion in a direction from the second light emitting portion toward the light receiving portion may be 0.5 mm or more and less than 2.0 mm.

In the biological information measurement device according to the second aspect, in the light receiving portion, a region having a distance of less than 2.0 mm to the second light emitting portion may be larger than a region having a distance of 2.0 mm or more to the second light emitting portion.

In the biological information measurement device according to the second aspect, the second light emitting portion may be disposed between the first light emitting portion and the light receiving portion.

In the biological information measurement device according to the second aspect, a plurality of the second light emitting portions may be provided by interposing the light receiving portion therebetween in a plan view, and a plurality of the first light emitting portions may be provided by interposing the plurality of second light emitting portions and the light receiving portion therebetween in a plan view.

In the biological information measurement device according to the second aspect, the light receiving portion may be positioned between the first light emitting portion and the second light emitting portion.

BRIEF DESCRIPTION OF THE DRAWINGS

FIG. 7 is a table illustrating a relationship between a distance between a light emission center of a second light emitting portion and a light reception center of the light receiving portion, quality of a second detection signal, and realizability of a disposition of the second light emitting portion and the light receiving portion in the first embodiment.

DESCRIPTION OF EXEMPLARY EMBODIMENTS

First Embodiment

Hereinafter, a first embodiment of the present disclosure will be described based on the drawings.
Schematic Configuration of Biological Information Measurement Device FIG. 1 is a front view illustrating a biological information measurement device 1 according to this embodiment.

The biological information measurement device 1 according to this embodiment is a wearable device that is worn on a user's body, which is a living body, and is used to measure biological information of the user. Specifically, the biological information measurement device 1 is a device that is worn on a user's wrist or other worn parts, detects a pulse wave that is one of biological information, and measures a pulse rate that is also one of biological information.

Figure 1:
FIG. 1 is a front view illustrating a biological information measurement device according to a first embodiment of the present disclosure.

As illustrated in FIG. 1, the biological information measurement device 1 includes a housing 2 and bands BN1 and BN2 provided on the housing 2. The housing 2 includes a front portion 21 having a display window 211 which allows the user to visually recognize biological information displayed on a display unit 51, and a back portion 22 which comes in contact with the user's body when the biological information measurement device 1 is worn (see FIG. 3).
Configuration of Band The band BN1 extends from one end of the housing 2 and the band BN2 extends from the other end of the housing 2 when viewed from a position facing the front portion 21. That is, the bands BN1 and BN2 extend from ends opposite to each other in the housing 2 in the directions away from each other. The housing 2 is worn on the worn part by connecting the bands BN1 and BN2 to each other by clasp (not illustrated). The bands BN1 and BN2 may be formed integrally with the housing 2.

In the following description, the direction from the front portion 21 toward the back portion 22 is taken as the +Z direction. The directions orthogonal to the +Z direction and orthogonal to each other are taken as the +X direction and the +Y direction. Although not illustrated, the −Z direction, the −X direction, and the −Y direction are opposite to the +Z direction, the +X direction, and the +Y direction, respectively.

In this embodiment, an extension direction of the band BN1 is the +Y direction when viewed from the −Z direction side. Further, the +X direction is a direction from the right toward the left when the biological information measurement device 1 is viewed from the −Z direction side so that the +Y direction is upward.

Among the directions described above, the +Z direction is also a direction in which a first light emitting portion 81 and a second light emitting portion 82 (see FIG. 3) described later mainly emit first light and second light, and is also a direction along the normal to the light receiving surface 831 of the light receiving portion 83 described later. Furthermore, the +Z direction is also a direction along the normal to a substrate 85 described later.

Hereinafter, viewing an object from the +Z direction side will be referred to as "in a plan view".

Configuration of Housing

The housing 2 includes a side portion 23 in addition to the front portion 21 and the back portion 22 (see FIG. 3) described above.

The display window 211 of the front portion 21 is closed by a light-transmitting cover 212.

The side portion 23 is an annular portion formed along the circumferential direction centered on the +Z direction, and couples the front portion 21 and the back portion 22. In a region on the −X direction side of the side portion 23, buttons 31 and 32 constituting an operation unit 3 are disposed and buttons 33 and 34 similarly constituting the operation unit 3 are disposed.

A configuration of the back portion 22 will be described in detail later.

Internal Configuration of Biological Information Measurement Device

Figure 2:
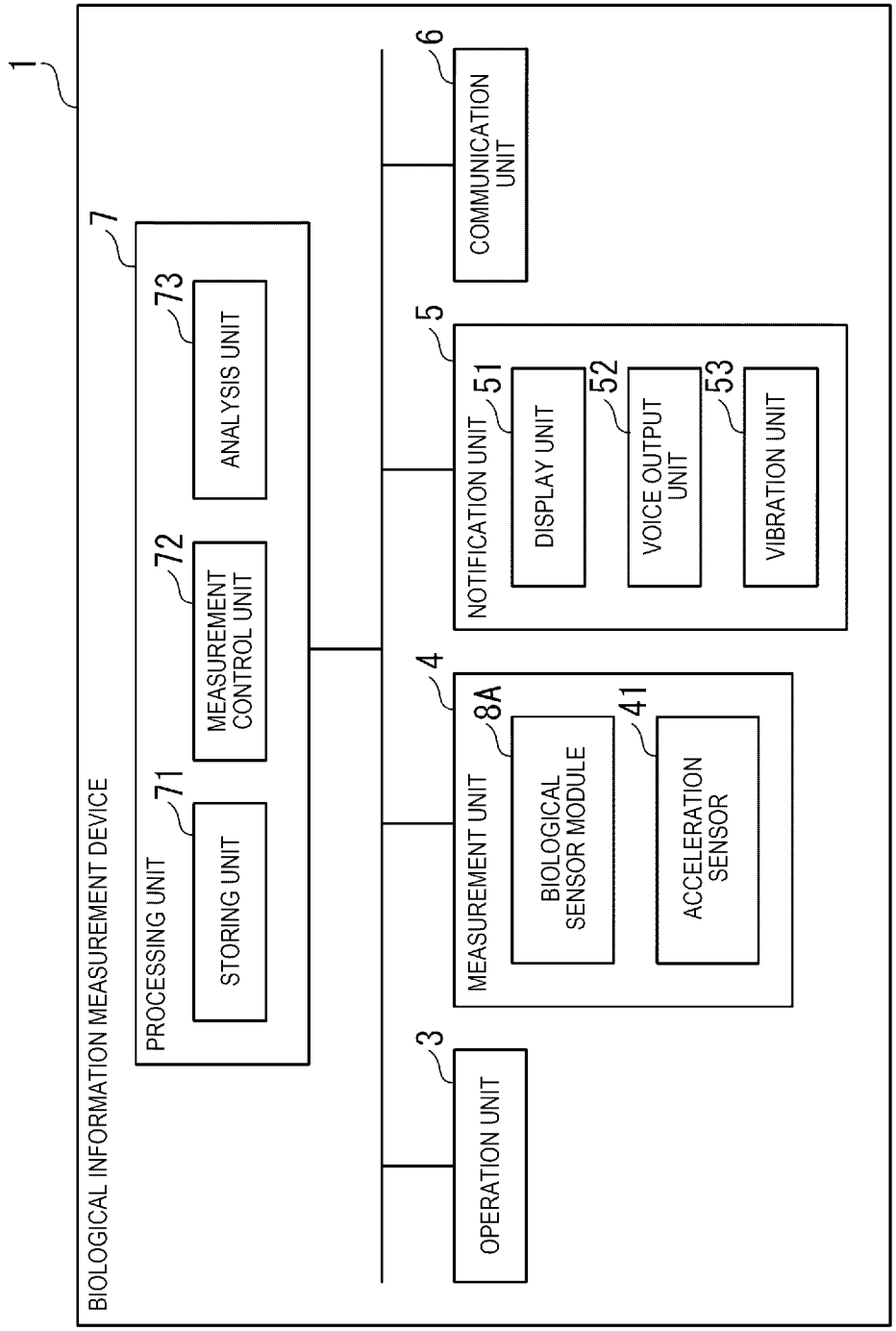
FIG. 2 is a block diagram illustrating a configuration of the biological information measurement device in the first embodiment.

FIG. 2 is a block diagram illustrating the configuration of the biological information measurement device 1.

As illustrated in FIG. 2, the biological information measurement device 1 further includes the operation unit 3, a measurement unit 4, a notification unit 5, a communication unit 6, and a processing unit 7 provided in the housing 2.

The operation unit 3 has the buttons 31 to 34, and outputs an operation signal according to the input of the button 31 to 34 to the processing unit 7.

The measurement unit 4 measures various pieces of information and outputs a measurement result to the processing unit 7. The measurement unit 4 includes a biological sensor module 8A that detects a pulse wave which is biological information, and an acceleration sensor 41 that detects acceleration acting on the biological information measurement device 1. The configuration of the biological sensor module 8A will be described in detail later.

The notification unit 5 notifies various pieces of information to the user under control of the processing unit 7. The notification unit 5 includes a display unit 51, a voice output unit 52, and a vibration unit 53.

The display unit 51 includes various display panels such as liquid crystal and electronic paper, and displays information input from the processing unit 7, for example, a pulse rate which is one of user's biological information.

The voice output unit 52 outputs a voice according to a voice signal input from the processing unit 7.

The vibration unit 53 includes a motor whose operation is controlled by the processing unit 7 and notifies, for example, a warning to the user by vibration generated by drive of the motor.

The communication unit 6 is a communication module that outputs information received from an external device to the processing unit 7 in addition to transmitting detected and analyzed biological information to an external device. In this embodiment, the communication unit 6 wirelessly communicates with an external device by the short distance wireless communication method, but may communicate with the external device through a relay device such as a cradle or a cable. Furthermore, the communication unit 6 may communicate with the external device through a network.

The processing unit 7 is configured by a circuit board having an arithmetic processing circuit and a flash memory, and is electrically coupled to the operation unit 3, the measurement unit 4, the notification unit 5, and the communication unit 6. The processing unit 7 controls the overall operation of the biological information measurement device 1 autonomously or according to an operation signal input from the operation unit 3. In addition, the processing unit 7 controls the biological sensor module 8A and the acceleration sensor 41 to analyze detection signals input from the biological sensor module 8A and the acceleration sensor 41.

The processing unit 7 includes a storing unit 71 configured by the flash memory, and a measurement control unit 72 and analysis unit 73 configured by the arithmetic processing circuit that executes a program stored in the storing unit 71.

The storing unit 71 stores various programs and data necessary for the operation of the biological information measurement device 1. The storing unit 71 stores a detection signal input from the measurement unit 4 and analysis result by the analysis unit 73.

The measurement control unit 72 controls the operation of the biological sensor module 8A.

The analysis unit 73 analyzes the detection signal input from the measurement unit 4 and calculates biological information such as the pulse rate. A pulse rate calculation process executed by the analysis unit 73 may be employed a known method.

Configuration of Back Portion of Housing

Figure 3:
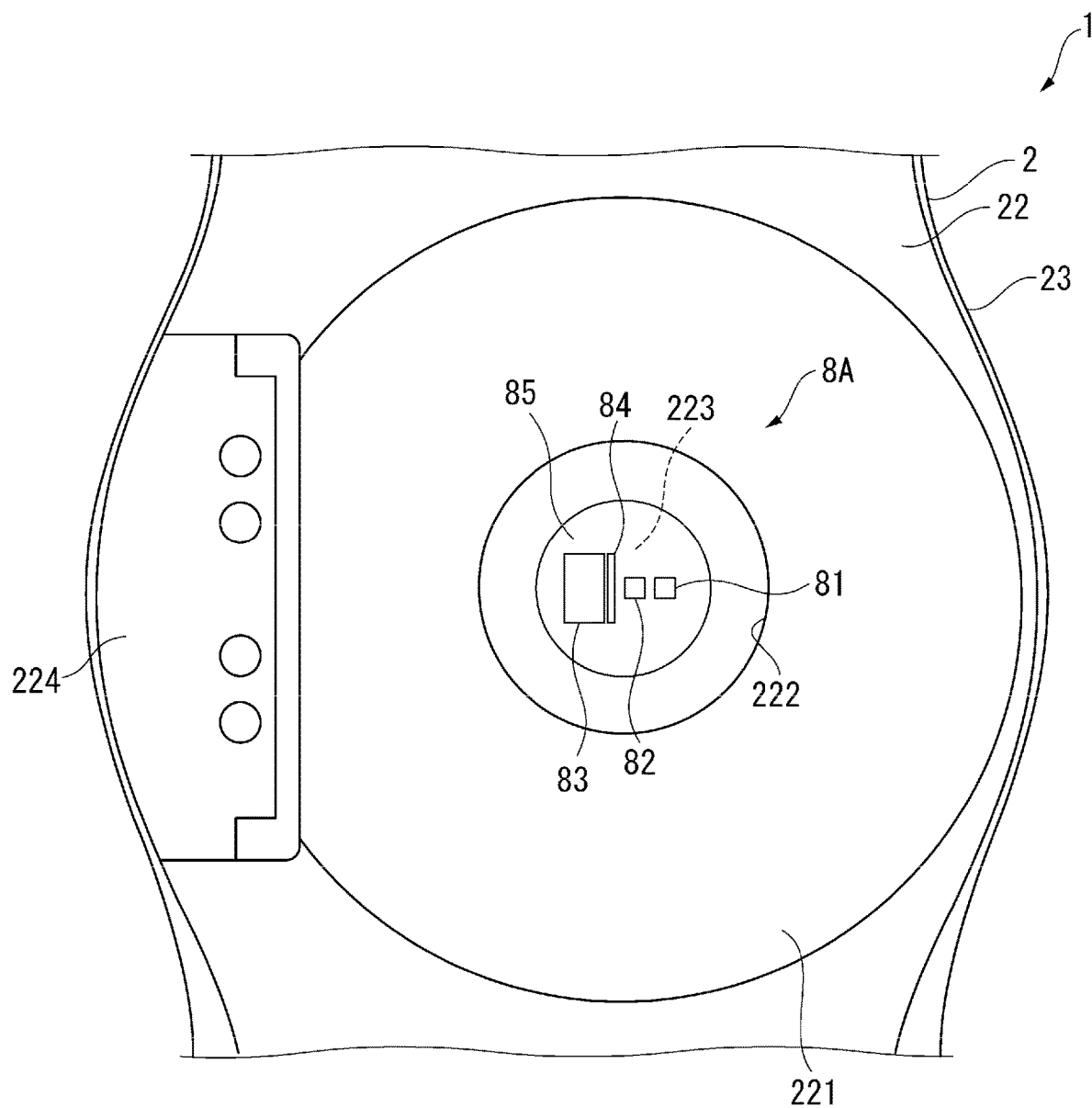
FIG. 3 is a plan view illustrating a back portion of a housing in the first embodiment.

FIG. 3 is a plan view illustrating the back portion 22 of the housing 2. In FIG. 3, illustration of the buttons 31 to 34 is omitted.

The back portion 22 includes a substantially circular contact portion 221 at substantially the center in a plan view. The contact portion 221 is formed in a convex shape that protrudes in the +Z direction toward the center in a plan view, and is a portion comes in contact with the user's body in the housing 2 when the biological information measurement device 1 is worn on the user's body. At the center of the contact portion 221, an opening 222 having a circular shape in a plan view is formed.

In the opening 222, a first light emitting portion 81, a second light emitting portion 82, a light receiving portion 83, and a light shielding portion 84 of the biological sensor module 8A described later are disposed. A light-transmitting member 223 is provided in the opening 222 and the opening 222 is closed by the light-transmitting member 223.

A coupling portion 224 connected to a cradle (not illustrated) is provided at a portion in the −X direction of the back portion 22.

Configuration of Biological Sensor Module

Figure 4:
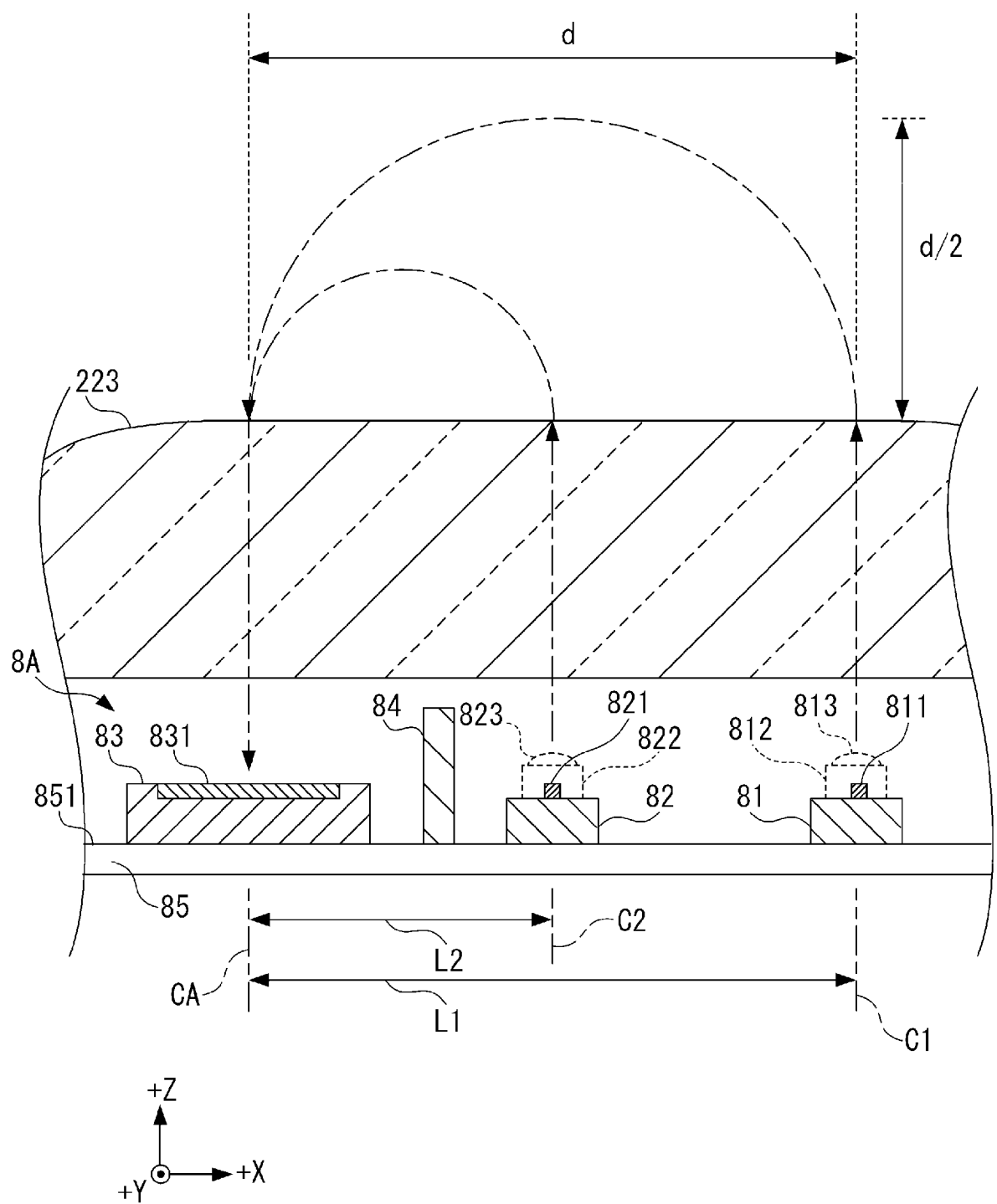
FIG. 4 is a cross-sectional view illustrating a biological sensor module according to the first embodiment.

FIG. 4 is a view illustrating a cross section of the biological sensor module 8A along the XZ plane.

The biological sensor module 8A detects a pulse wave which is one of the biological information. As illustrated in FIGS. 3 and 4, the biological sensor module 8A includes the first light emitting portion 81, the second light emitting portion 82, the light receiving portion 83, the light shielding portion 84, and the substrate 85 on which these units are provided.

The substrate 85 is provided in the housing 2 and supports the first light emitting portion 81, the second light emitting portion 82, the light receiving portion 83, and the light shielding portion 84 on a surface 851 on the +Z direction side. The substrate 85 supplies power to the first light emitting portion 81 and the second light emitting portion 82, and outputs a detection signal output from the light receiving portion 83 to the processing unit 7 through a connector (not illustrated) according to an amount of received light. The substrate 85 may be a rigid substrate or may be a flexible printed circuit (FPC).

The first light emitting portion 81 emits first light to be irradiated to the user's body which is a living body, and the second light emitting portion 82 emits second light irradiated to the user's body.

Specifically, the first light emitting portion 81 emits light having a wavelength of 500 nm or more and less than 600 nm as the first light, and the second light emitting portion 82 emits light having a wavelength of 600 nm or more as the second light. Specifically, the second light is light having a wavelength of 600 nm or more and 940 nm or less. In this embodiment, the first light is green light which is light having a wavelength of 500 nm or more and 570 nm or less and with which a pulse wave is capable of being detected, and the second light is red light which is light having a wavelength of 600 nm or more and 650 nm or less and with which movement of the skin of the worn part is capable of being detected.

As illustrated in FIG. 4, the first light emitting portion 81 is an LED chip including a light emitting element 811 such as a light emitting diode (LED), sealing resin 812 for sealing the light emitting element 811, and a lens 813 for condensing light emitted from the light emitting element 811. Similarly, the second light emitting portion 82 is an LED chip having a light emitting element 821, sealing resin 822 and a lens 823. However, the light emitting element is not limited to an LED chip, and at least one of the first light emitting portion 81 and the second light emitting portion 82 may be a bare chip in which the light emitting element is not sealed by sealing resin.

The first light emitting portion 81 and the second light emitting portion 82 are arranged side by side in the +X direction in a plan view as illustrated in FIGS. 3 and 4, and the second light emitting portion 82 is disposed between the first light emitting portion 81 and the light receiving portion 83. In other words, the first light emitting portion 81, the second light emitting portion 82, and the light receiving portion 83 are arranged in the order of the first light emitting portion 81, the second light emitting portion 82, and the light receiving portion 83 in the −X direction in a plan view. That is, the first light emitting portion 81 is positioned on the side opposite to the light receiving portion 83 with respect to the second light emitting portion 82.

In the following description, the term of "light emission center of the first light emitting portion" refers to the center of the light emitting element in the first light emitting portion in a plan view. Similarly, the term of "light emission center of the second light emitting portion" refers to the center of the light emitting element in the second light emitting portion in a plan view. In this embodiment, a light emission center C1 of the first light emitting portion 81 coincides with the center of the first light emitting portion 81 in a plan view, and a light emission center C2 of the second light emitting portion 82 coincides with the center of the second light emitting portion 82 in a plan view.

The light receiving portion 83 receives the first light and the second light respectively reflected by the user's body. Although described later in detail, the light receiving portion 83 receives the second light reflected by the user's epidermis and dermis, in addition to receiving the first light reflected by the user's epidermis, dermis, and subcutaneous layer. Then, the light receiving portion 83 outputs a first detection signal indicating an amount of received first light and a second detection signal indicating the amount of received the second light. The first detection signal is a signal output based on the first light received by the light receiving portion 83, and the second detection signal is a signal output based on the second light received by the light receiving portion 83.

Although detailed illustration is omitted, the light receiving portion 83 is a photodiode (PD) chip in which a light receiving element is sealed by the sealing resin. However, the light receiving portion is not limited to the PD chip, and the light receiving portion 83 may be a bare chip in which the light receiving element is not sealed by resin.

The light receiving element includes, for example, an n-type semiconductor region on the silicon substrate side and a p-type semiconductor region on the light receiving surface side, and outputs the current as a detection signal by the power effect when light having sufficiently large energy is incident on the p-type semiconductor region. A light receiving surface 831 which is an active area in the light receiving portion 83 is a part where the p-type semiconductor region is positioned in a plan view.

In the following description, the term of "the light reception center of the light receiving portion" refers to the center of the light receiving surface in the light receiving portion in a plan view. In this embodiment, the light reception center CA of the light receiving portion 83 coincides with the center of the light receiving portion 83 in a plan view.

Although not illustrated, such a light receiving portion 83 includes a wavelength limiting filter which transmits light in a wavelength band including the wavelength of the first light and the wavelength of the second light, restricts transmission of light other than the wavelength band, and limits the wavelength of light incident on the light receiving surface 831.

In addition, the light receiving portion 83 has an angle limiting filter that transmits the light if an incident angle of the light with respect to the normal to the light receiving surface 831 is less than a predetermined angle, and restricts transmission of the light if the incident angle is equal to or greater than the predetermined angle.

The light shielding portion 84 is disposed between the second light emitting portion 82 and the light receiving portion 83, and shields the first light directed from the first light emitting portion 81 directly to the light receiving portion 83 and the second light directed from the second light emitting portion 82 to the light receiving portion 83 to suppress the first light and the second light from being directly incident on the light receiving portion 83 without passing through the user's body.

In this embodiment, the light shielding portion 84 is configured by a plate-like body such as a wall standing up from the surface 851. However, the light shielding portion is not limited to the plate-like body and may be configured in a frame shape surrounding four sides of the light receiving portion 83 in a plan view.

Figure 5:
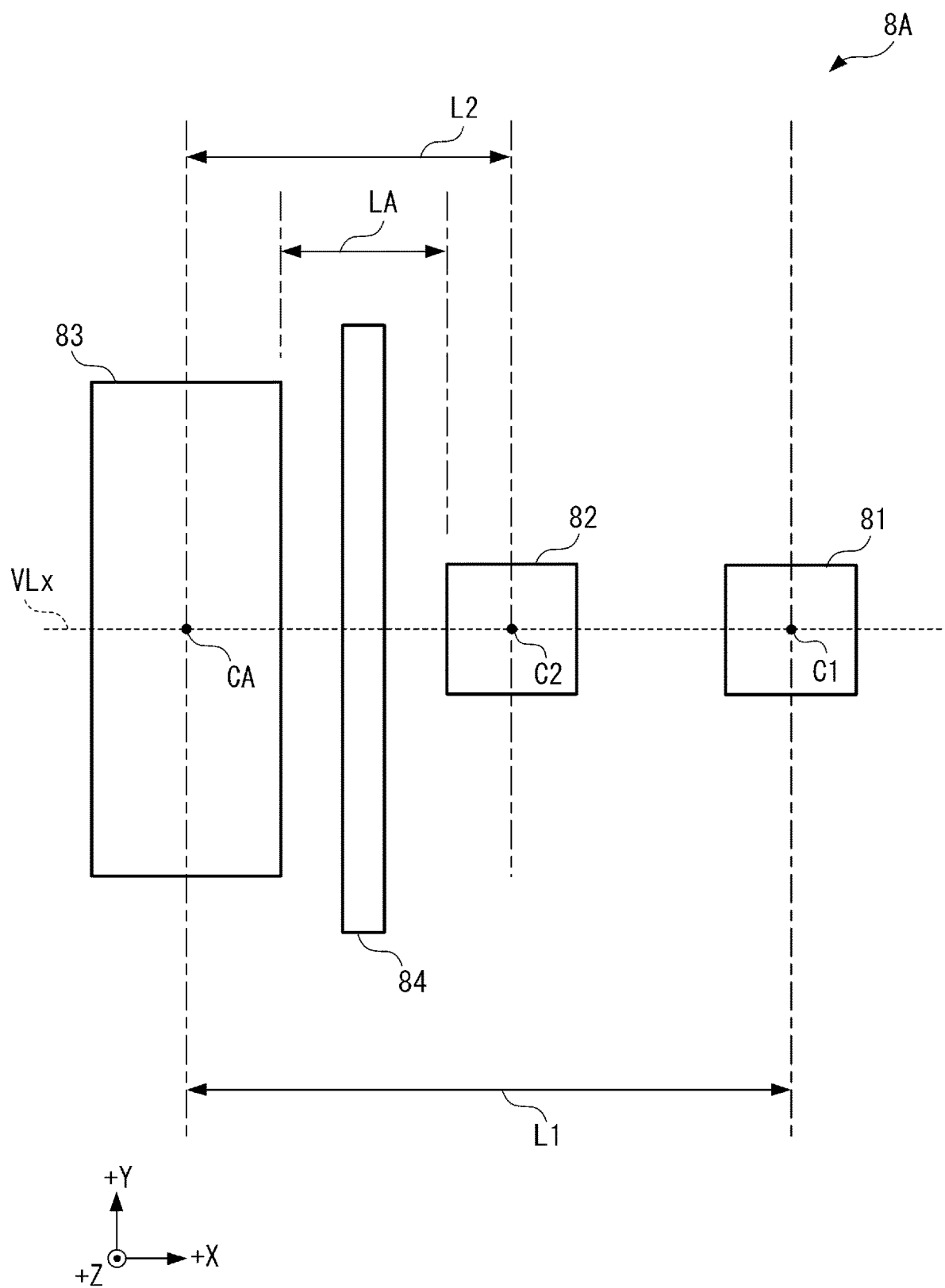
FIG. 5 is a plan view illustrating the biological sensor module in the first embodiment.

Disposition of First Light Emitting Portion, Second Light Emitting Portion, and Light Receiving Portion FIG. 5 is a plan view illustrating the biological sensor module 8A. In FIG. 5, illustration of the substrate 85 is omitted.

As described above, the light receiving portion 83 is disposed on the side opposite to the first light emitting portion 81 with respect to the second light emitting portion 82. As illustrated in FIG. 5, the light emission center C2 of the second light emitting portion 82 and the light emission center C1 of the first light emitting portion 81 are positioned on an virtual line VLx parallel to the +X direction and passing through the light reception center CA of the light receiving portion 83.

Here, as illustrated in FIGS. 4 and 5, a distance L2 between the light reception center CA and the light emission center C2 in the +X direction in which the light receiving portion 83 and the second light emitting portion 82 are arranged side by side is shorter than a distance L1 between the light reception center CA and the light emission center C1 in the +X direction in which the light receiving portion 83 and the first light emitting portion 81 are arranged side by side. Specifically, the distance L1 is a value in the range of more than 2.0 mm and 5.0 mm or less, whereas the distance L2 is a value in the range of less than 2.0 mm.

Specifically, the distance L2 is set to a value within the range of 0.5 mm or more and less than 2.0 mm. The distance L2 is preferably a value within the range of 0.8 mm or more and less than 2.0 mm, more preferably a value within the range of 0.8 mm or more and 1.5 mm or less.

The reason for setting the distances L1 and L2 in this way is as follows.

Figure 6:
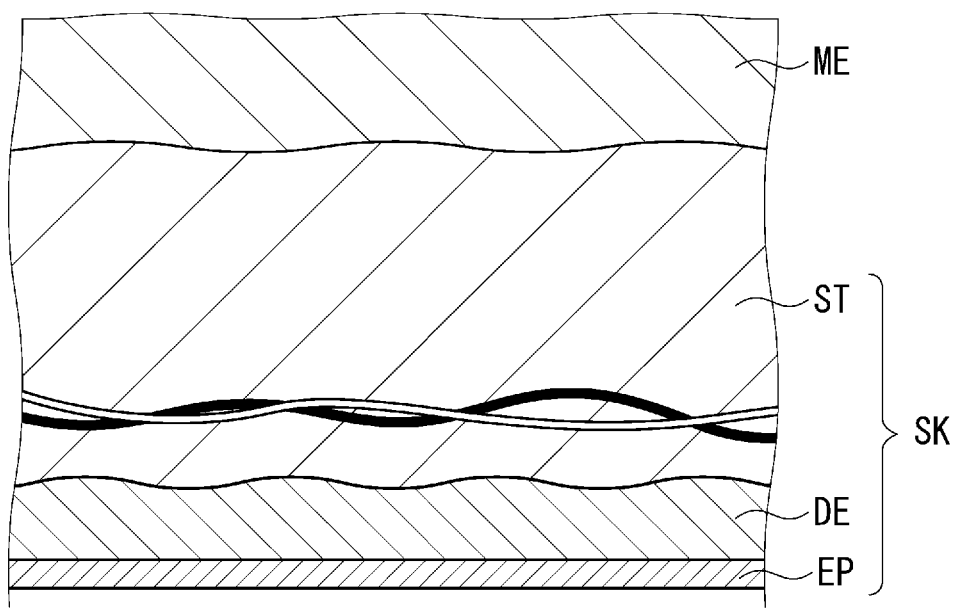
FIG. 6 is a cross-sectional view illustrating a worn part of a user in the first embodiment.

Reason for Disposition of First Light Emitting Portion, Second Light Emitting Portion, and Light Receiving Portion FIG. 6 is a cross-sectional view illustrating a user's wrist as an example of a user's body on which the biological information measurement device 1 is worn part. In detail, FIG. 6 is a view illustrating a cross section along the YZ plane of the user's wrist.

The wrist on which the biological information measurement device 1 is worn includes a skin SK and a muscle layer ME covered by the skin SK, as illustrated in FIG. 6.

The skin SK mainly has a three-layered layer structure. Specifically, the skin SK is composed of an epidermis EP that constitutes the uppermost layer, a dermis DE covered by the epidermis EP, and a subcutaneous layer ST that constitutes the lowermost layer and is covered by the dermis DE.

The epidermis EP is a region having a thickness of 0.06 mm or more and 0.2 mm or less, and nerves reach the epidermis EP.

The dermis DE is a region having a thickness of 0.2 mm or more and 2.2 mm or less, and capillaries exist in the dermis DE.

The subcutaneous layer ST is a layer positioned below the dermis DE, and includes subcutaneous fat and subcutaneous tissue. Specifically, the subcutaneous layer ST is a connective tissue between the dermis DE and the bone and muscle layers, and is covered by the dermis DE. The subcutaneous fat mainly consists of fat cells, and blood vessels including arteries and veins and nerves are positioned in the subcutaneous tissue.

The muscle layer ME is a part where the muscle is positioned, and an extensor digitorum muscle is positioned in the muscle layer ME of the wrist. The extensor digitorum muscle is a muscle that stretches and flexes four fingers except the thumb. When moving a finger, for example, when performing a gooper exercise that repeats an action of holding a hand and an action of opening, or when performing a tapping movement that strikes a keyboard, since the extensor digitorum muscle contracts and stretches, movement of the extensor digitis muscle displaces the skin SK.

Here, the first light and the second light with which the living body travel is irradiated travel in the living body, are reflected and scattered in the living body, and are emitted out of the living body.

The first light, which is green light, is light that is easily absorbed by blood. For that reason, since the first light incident on the living body changes with a flow rate of blood flowing in the capillary, that is, due to pulsation of a blood vessel, the amount of first light received by the light receiving portion 83 also changes similarly.

However, the degree of light scattering in the living body changes depending on displacement of the skin SK. That is, when the skin SK is displaced due to the movement of the extensor digitorum muscle or the like, light scattering occurs in many directions in the living body, and the amount of received light changes due to an element that is not a change according to the pulsation of the blood vessel. Thus, when the skin SK is displaced, the first detection signal output from the light receiving portion 83 is likely to include a noise component associated with the displacement of the skin SK.

On the other hand, the second light which is red light is light which is difficult to be absorbed by blood. For that reason, while the second light incident on the living body is not susceptible to the absorption according to the pulsation of the blood vessel, the second light is scattered in the living body in the same manner as the first light. That is, the change in the amount of received second light can be regarded as the change due to the movement of the skin SK. A second detection signal according to the amount of received second light is used as a reference signal for the noise component and a first detection signal according to the amount of received first light is subjected to adaptive filter processing to remove the noise component from the first detection signal, thereby capable of extracting the pulsation component.

As illustrated in FIG. 4, it can be inferred, from the distance between an irradiation position of light on the surface of the epidermis EP which is a part of the living body and an emission position of light from the surface of the epidermis EP, how deep the light incident on the living body and emitted from the living body passes from the surface of the skin SK.

Specifically, assuming that the distance between the irradiation position and the emission position is d (mm), the light with which the irradiation position is irradiated reaches a part of a depth of approximately d/2 (mm) from the surface of the epidermis EP and then, is emitted from the emission position. For example, when the distance between the irradiation position and the emission position is 2 mm, the light with which the irradiation position is irradiated reaches parts of a depth of 1 mm from the surface of the epidermis EP, that is, the epidermis EP and the dermis DE, and is emitted after being reflected by the epidermis EP and the dermis DE.

For that reason, the irradiation position and the emission position of the second light which is red light, that is, the light emission center C2 of the second light emitting portion 82 which emits the second light in the +Z direction and the light reception center CA of the light receiving portion 83 is set at a position where the ratio of the amount of received second light which is reflected in the vicinity of the epidermis EP and the dermis DE and is received by the light receiving portion 83 is dominant in the amount of light received by the light receiving portion 83, thereby capable of allowing the second detection signal output from the light receiving port ion 83 to be a signal indicating noise according to the displacement of the skin SK due to the movement of the extensor digitorum muscle.

FIG. 7 is a table illustrating the relationship between the distance L (mm) between the light emission center C2 of the second light emitting portion 82 and the light reception center CA of the light receiving portion 83 in the +X direction, quality of the second detection signal and realizability of the disposition of the second light emitting portion 82 and the light receiving portion 83. In FIG. 7, regarding signal quality and realizability, A or a is attached when it is "excellent", B orb is attached when it is for "good", C or c is attached when it is "possible", and D or d when it is "not possible".

When the signal quality is "excellent (A)", it is indicated that a clear peak according to the movement of the skin SK appears in a waveform of the second detection signal, and when the signal quality is "good (B)", it is indicated that a peak according to the movement of the skin SK appears in the waveform of the second detection signal. When the signal quality is "possible (C)", it is indicated that a waveform according to the movement of the skin SK is included in the waveform of the second detection signal, and when the signal quality is "not possible (D)", it is indicated that the waveform according to the movement of the skin SK is not included in the waveform of the second detection signal.

On the other hand, when realizability is "excellent (a)", it is indicated that the disposition of the second light emitting portion 82 and the light receiving portion 83 on the substrate 85 can be easily implemented, and when realizability is "good (b)", it is indicated that the disposition can be implemented although it is not easy. When realizability is "possible (c)", it is indicated that the disposition of the second light emitting portion 82 and the light receiving portion 83 on the substrate 85 is possible but not impossible, and the when realizability is "not possible (d)", it is indicated that the disposition of the second light emitting portion 82 and the light receiving portion 83 is difficult due to the problem of the size of the element and the like.

As illustrated in FIG. 7, when the distance L was less than 2.0 mm, the signal quality of the noise signal was "good" or more.

In detail, when the distance L is a value within the range of 0.3 mm or more and less than 2.0 mm, since signal intensity of the second detection signal is "good" or more, a noise component accompanying the movement of the skin SK can be effectively removed from the first detection signal using the second detection signal.

When the distance L is a value within the range of 0.5 mm or more and less than 2.0 mm, since the signal intensity of the second detection signal is "good" or more, and realizability is "good" or more, the noise component accompanying the movement of the skin SK can be effectively removed from the first detection signal using the second detection signal and the disposition of the second light emitting portion 82 and the light receiving portion 83 can be realized.

When the distance L is a value within the range of 0.8 mm or more and less than 2.0 mm, the noise component can be effectively removed, and the disposition of the second light emitting portion 82 and the light receiving portion 83 can be easily implemented.

When the distance L is a value within the range of 0.8 mm or more and 1.5 mm or less, since the signal intensity and realizability are respectively "excellent", the noise component can be more effectively removed, and the disposition of the second light emitting portion 82 and the light receiving portion 83 can be easily implemented.

From the result described above, in order to enhance the signal quality of the second detection signal, the second light emitting portion 82 is preferably disposed with respect to the light receiving portion 83 such that the distance L2 between the light emission center C2 of the second light emitting portion 82 and the light reception center CA of the light receiving portion 83 has a value in a range of less than 2 mm, in the +X direction, which is a direction in which the second light emitting portion 82 is aligned with the light receiving portion 83.

When considering realizability, the distance L2 is preferably a value within the range of 0.3 mm or more and less than 2.0 mm, and more preferably a value within the range of 0.8 mm or more and less than 2.0 mm. Furthermore, the distance L2 is preferably a value within the range of 0.8 mm or more and 1.5 mm or less.

On the other hand, when the distance L1 is longer than the distance L2, the first light emitted from the first light emitting portion 81 travels deep in the user's body, the amount of light absorption by blood increases, and change in the amount of received light according to pulsation becomes large. When the distance L1 is 2.0 mm or more, the first light easily passes through the epidermis EP to reach the blood vessel positioned in the dermis DE or the subcutaneous layer ST, and the influence of the light absorption by the blood increases. On the other hand, when the distance L1 is less than 2.0 mm, it becomes difficult for the first light to reach the capillary, and when the distance L1 exceeds 5.0 mm, the first light reaches the muscle layer ME, the degree of scattering of the first light increases, and a ratio of a pulsation component to the change in the amount of received light decreases, which makes it difficult to obtain the pulsation component. For that reason, the distance L1 is set as described above. In this case, the first light received by the light receiving portion 83 is the first light reflected by the epidermis EP, the dermis DE and the subcutaneous layer ST. However, the distance L1 can be changed as appropriate.

Space Between Second Light Emitting Portion and Light Receiving Portion

In order to effectively cause the second light emitted from the second light emitting portion 82 and reflected by the user's body to be incident on the light receiving portion 83 on the premise of the distance between the light emission center C2 of the second light emitting portion 82 and the light reception center CA of the light receiving portion 83 as described above, the distance LA between an end on the light receiving portion 83 side in the second light emitting portion 82 and an end on the second light emitting portion 82 side in the light receiving portion 83 in the +X direction is set as follows.

Figure 8:
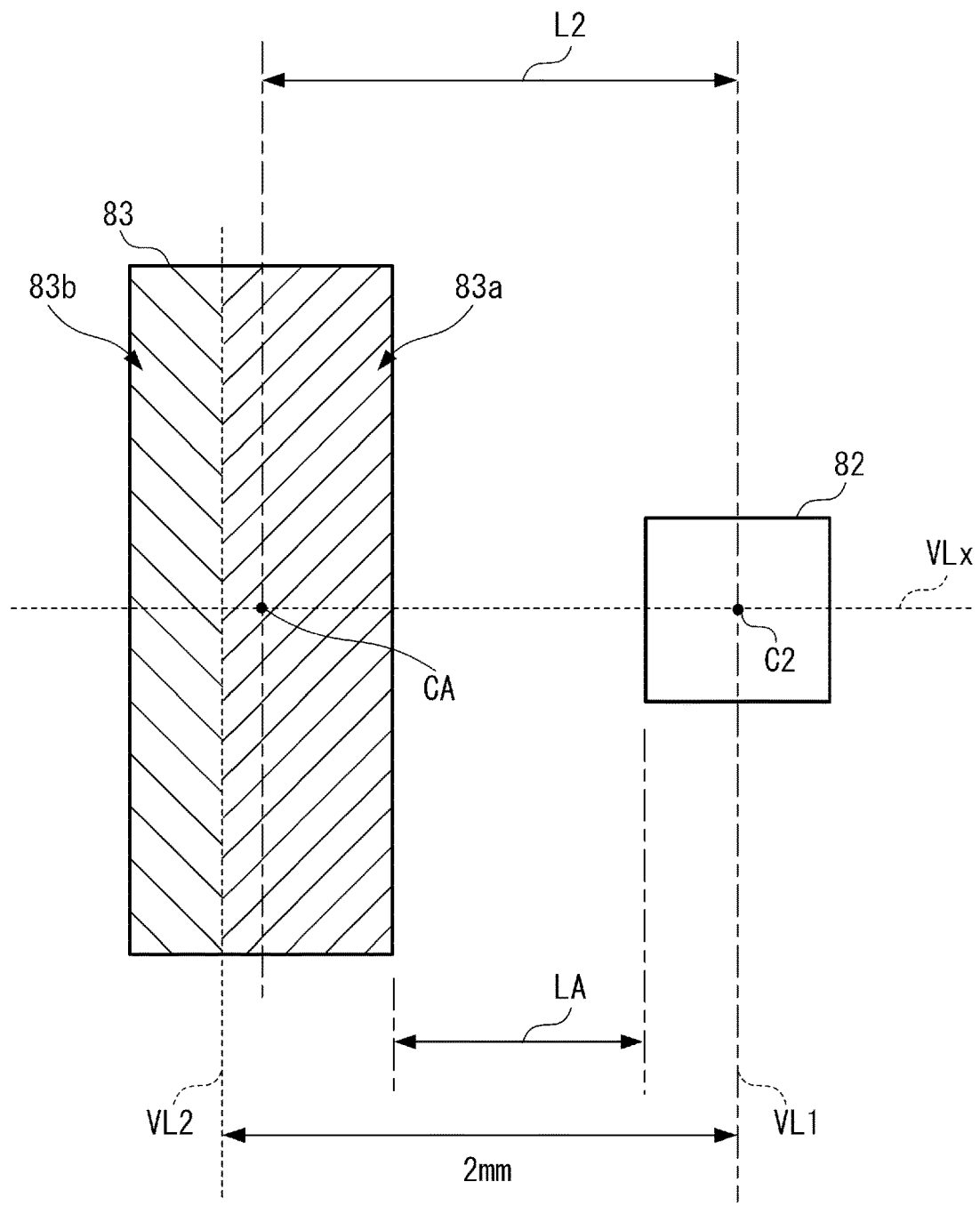
FIG. 8 is a plan view illustrating a space between the second light emitting portion and the light receiving portion in the first embodiment.

FIG. 8 is a plan view illustrating the space between the second light emitting portion 82 and the light receiving portion 83. In FIG. 8, the first light emitting portion 81 and the light shielding portion 84 are not illustrated.

First, as illustrated in FIG. 8, a virtual line parallel to the +Y direction orthogonal to the +X direction in which the second light emitting portion 82 and the light receiving portion 83 are arranged, and passing through the light emission center C2 is a virtual line VL1. Further, a virtual line parallel to the virtual line VL1 and separated by 2 mm from the virtual line VL1 toward the light receiving portion 83 is a virtual line VL2. Then, a light receiving surface 831 of the light receiving portion 83 is virtually divided into a first region 83a which is a region on the second light emitting portion 82 side, and a second region 83b which is a region opposite to the second light emitting portion 82 by the virtual line VL2 in a plan view. That is, the first region 83a is a region separated by less than 2 mm from the virtual line VL1, and the second region 83b is a region separated by 2 mm or more from the virtual line VL1.

When the light receiving surface 831 is divided as described above, if the area of the first region 83a in a plan view is equal to or larger than the area of the second region 83b in a plan view, the second light emitted from the second light emitting portion 82 and mainly reflected by the dermis DE is easily received by the light receiving portion 83.

An area of the first region 83a in a plan view can be made equal to or larger than area of the second region 83b in a plan view by setting the distance LA between the end of the second light emitting portion 82 on the light receiving portion 83 side and the end of the light receiving portion 83 on the second light emitting portion 82 side in the +X direction as a value within the range of 0.01 mm or more and 1.00 mm or less. With this configuration, the second light reflected by the dermis DE can be easily received by the light receiving portion 83. Accordingly, the signal intensity and signal quality of the second detection signal can be enhanced, and noise components can be easily removed from the first detection signal.

FFT Analysis Result of First Detection Signal and Second Detection Signal

Figure 9:
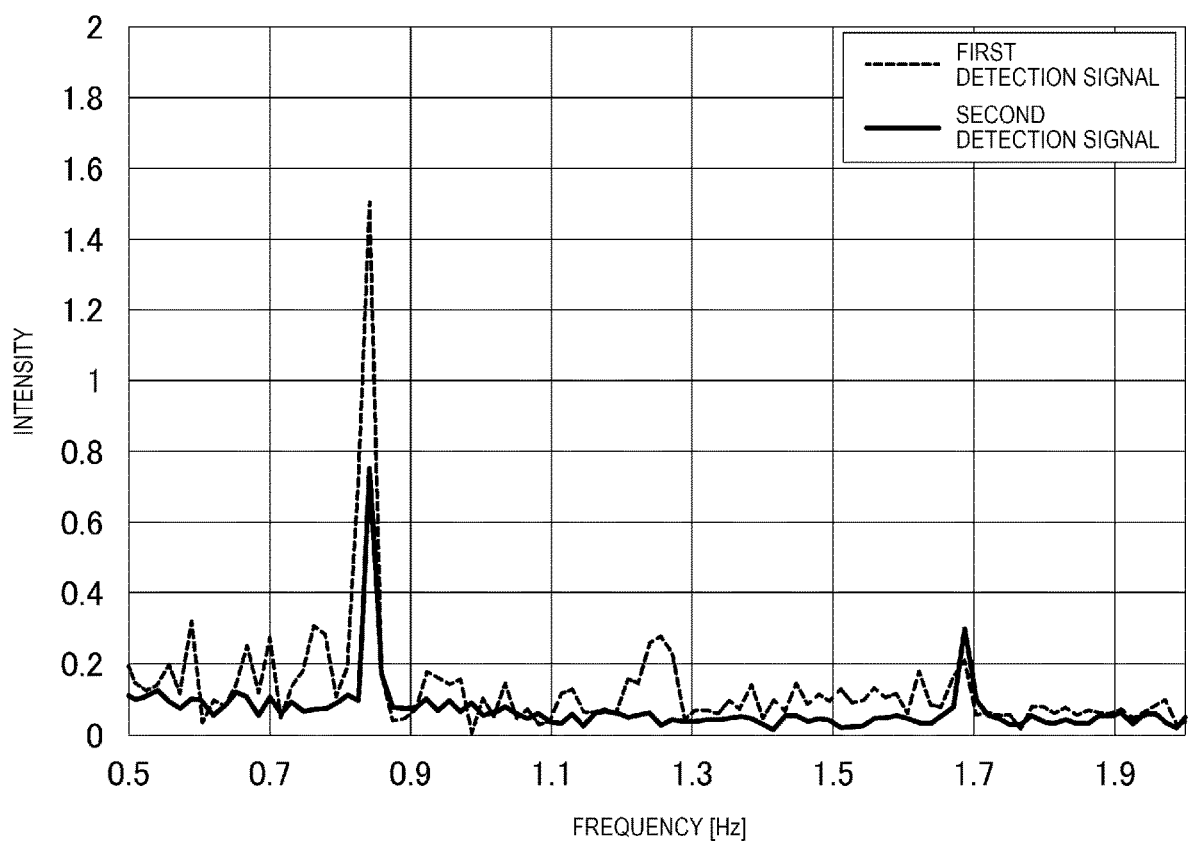
FIG. 9 is a graph illustrating an example of an FFT analysis result of the first detection signal and the second detection signal in the first embodiment.

FIG. 9 is a graph illustrating an example of analysis result by the fast Fourier transform (FFT) on the first detection signal and the second detection signal. In FIG. 9, the dotted line indicates the FFT analysis result of the first detection signal, and the solid line indicates the FFT analysis result of the second detection signal.

FIG. 9 illustrates the FFT analysis results of the first detection signal and the second detection signal when the second light emitting portion 82 is disposed at a position where the distance L2 is 1.0 mm and the first light emitting portion 81 is disposed at a position where the distance L1 is 2.0 mm. In addition, when the first light and the second light are received by the light receiving portion 83, the gooper exercise described above is performed at a period of 0.8 Hz.

As illustrated by the solid line in FIG. 9, in the FFT analysis result of the second detection signal, peaks appear at positions near 0.8 Hz and 1.6 Hz. Among these peaks, the peak at 0.8 Hz is a peak corresponding to the gooper exercise, and the peak at 1.6 Hz is a second harmonic when a frequency of the gooper exercise is taken as a fundamental wave.

On the other hand, as illustrated by the dotted line in FIG. 9, in the FFT analysis result of the first detection signal, peaks appear at positions near 0.8 Hz, 1.25 Hz, and 1.6 Hz. The peaks at 0.8 Hz and 1.6 Hz are peaks corresponding to the gooper exercise similarly as in the second detection signal. In contrast, the peak at 1.25 Hz corresponds to the pulsation.

From this result, it can be seen that the second detection signal contains no pulsation component.

When the processing unit 7 applies adaptive filter processing to the first detection signal using such a second detection signal as a reference signal for removing the noise component due to movement of the skin SK from the first detection signal, it can be seen that the noise components originating from the components other than pulsation, for example, the gooper exercise, can be removed from the first detection signal, and the pulsation component can be effectively acquired. Then, the processing unit 7 analyzes the first detection signal from which the noise component has been removed, thereby capable of calculating an accurate pulse rate.

As described above, a flow of venous blood is also affected by inertial motion, such as swinging an arm. That is, the first detection signal contains a noise component due to body motion in addition to the movement of the skin SK. Such a noise component can be removed by using an acceleration signal detected by the acceleration sensor 41 as a reference signal for noise removal. A known technique can be applied to removal of the noise component from the first detection signal using such an acceleration signal.

Effect of First Embodiment

With the biological information measurement device according to this embodiment described as above, the following effects can be exhibited.

Here, in the detection signal output from the light receiving portion that has received the first light reflected by the living body, not only the noise component caused by the movement of the worn part of the biological information measurement device in the user but also the noise component caused by the movement of the tissue at the worn part are contained. For example, when the biological information measurement device is worn on the user's wrist, the first detection signal not only contains the noise component according to movement of the wrist, the arm, or the entire body, but also the noise component corresponding to movement of the tissue such as the skin accompanying movement of the finger. Therefore, it has been newly found that more accurate biological information can be measured by removing the noise components accompanying movement of the tissue such as skin in use mode of a biological information processing device in which the movement of the finger occurs. However, an acceleration sensor and a pressure sensor are not suitable for acquiring the noise component accompanying the movement of tissues such as the skin.

In contrast, the biological information measurement device 1 includes the first light emitting portion 81 that emits the first light, the second light emitting portion 82 that emits the second light, the light receiving portion 83 that receives the first light reflected by the epidermis EP, dermis DE, and subcutaneous layer ST of the user, and the second light reflected by the epidermis EP and dermis DE of the user, and the processing unit 7 that calculates the pulse rate which is one of biological information by removing noise component, from the first detection signal output based on the first light received by the light receiving portion 83, using the second detection signal output based on the second light received by the light receiving portion 83.

According to this, since the second light emitted from the second light emitting portion 82 is light of a wavelength at which the movement of the skin SK can be easily detected, the second detection signal corresponding to the amount of received second light can be said to be a detection signal containing the noise component according to the movement of the skin SK. Then, the processing unit 7 removes the noise component from the first detection signal using the second detection signal, so that the noise component according to the movement of the skin SK can be effectively removed from the first detection signal. Accordingly, a component related to biological information, for example, a pulse wave component can be efficiently acquired.

On the other hand, when it is intended to detect movement of the skin SK by an acceleration sensor or a pressure sensor, the movement of the skin SK will be illustrated by an acceleration signal or a pressure signal. The physical quantities indicated by these signals are different from the amount of received light, which is the physical quantity indicated by the first detection signal. For that reason, the acceleration signal or the pressure signal is not suitable for the reference signal to be referred to when removing the noise component due to the movement of the skin SK from the first detection signal.

In contrast, since the second detection signal is a signal corresponding to the amount of light received by the light receiving portion 83 similarly to the first detection signal, the physical quantities indicated by the first detection signal and the second detection signal are the same. For that reason, the noise component can be effectively removed from the first detection signal by using the second detection signal, as compared to the case where the noise component is removed using the acceleration signal or the pressure signal.

Accordingly, measurement accuracy of the biological information by the biological information measurement device 1 can be enhanced.

The first light emitting portion 81 and the second light emitting portion 82 are disposed at positions where the path of the second light in the user's body is included in the path of the first light in the user's body. Specifically, the light emission center C1 of the first light emitting portion 81 and the light emission center C2 of the second light emitting portion 82 are positioned on a virtual line VLx passing through the light reception center CA of the light receiving portion 83, and the second light emitting portion 82 is positioned between the first light emitting portion 81 and the light receiving portion 83. For that reason, the path of the second light emitted from the second light emitting portion 82 and reflected by the epidermis EP and dermis DE of the user and incident on the light receiving portion 83 is included in the path of the first light emitted from the first light emitting portion 81 and reflected by the epidermis EP, the dermis DE, and the subcutaneous layer ST of the user and incident on the light receiving portion 83.

According to this, the noise component due to the movement of the skin SK at the part where the first light reaches in the user's body can be represented by the second detection signal. For that reason, the noise component due to the movement of the skin SK can be effectively removed from the first detection signal using the second detection signal. Accordingly, the measurement accuracy of biological information by the biological information measurement device 1 can be further enhanced.

The wavelength of the first light is 500 nm or more and less than 600 nm, and the wavelength of the second light is 600 nm or more. According to this, the first light can be light of a wavelength at which a pulse wave can be easily detected, and the second light can be light of a wavelength at which the movement of the skin SK can be easily detected. Accordingly, using the second detection signal, the noise component due to the movement of the skin SK can be effectively removed from the first detection signal, and the detection accuracy and measurement accuracy of the pulse wave which is one of the biological information by the biological information measurement device 1 can be further enhanced.

The distance between the second light emitting portion 82 and the light receiving portion 83 is less than 2.0 mm. That is, the biological information measurement device 1 includes the first light emitting portion 81 that emits the first light, the second light emitting portion 82 that emits the second light, the light receiving portion 83 that receives light from the first light emitting portion 81 and the second light emitting portion 82 and outputs the first detection signal and the second detection signal, and the processing unit 7 that determines the pulse rate which is one of biological information based on the first detection signal and the second detection signal, and the distance between the second light emitting portion 82 and the light receiving portion 83 is less than 2 mm.

According to this, the distance between the irradiation position to the living body of the second light emitted from the second light emitting portion 82 along the normal direction of the substrate 85 and the emission position of light, which enters the living body from the irradiation position, is reflected by the epidermis EP and the dermis DE positioned in a region less than 1.0 mm depth from the surface of the epidermis EP, and is incident into the light receiving portion 83, from the surface of the epidermis EP can be made less than 2.0 mm. For that reason, the ratio of the amount of received second light which is reflected by the epidermis EP and the dermis DE of the living body and is received by the light receiving portion 83 can be enhanced in the amount of light received by the light receiving portion 83. With this configuration, the movement of the skin SK of the user can be effectively detected by the second detection signal output from the light receiving portion 83 according to the amount of received second light. Accordingly, by using the second detection signal, the noise component due to the movement of the skin SK can be effectively removed from the first detection signal.

Also, as described above, the physical quantities indicated by the first detection signal and the second detection signal are the same. For that reason, by using the second detection signal, the noise component can be effectively removed from the first detection signal as compared to the case where the noise component is removed using the acceleration signal or the pressure signal.

Accordingly, the detection accuracy of biological information can be improved.

The distance between the second light emitting portion 82 and the light receiving portion 83 is the distance between the light emission center C2 of the second light emitting portion 82 and the light reception center CA of the light receiving portion 83. According to this, the positional relationship between the second light emitting portion 82 and the light receiving portion 83 can be set more clearly. In addition, the light receiving portion 83 can easily receive the second light reflected by the epidermis EP and dermis DE of the user.

The light emission center C2 of the second light emitting portion 82 is the center of the second light emitting portion 82 in a plan view, and the light reception center CA of the light receiving portion 83 is the center of the light receiving surface 831 of the light receiving portion 83 in a plan view. According to this, when the second light emitting portion 82 and the light receiving portion 83 are disposed such that the distance L2 becomes a value within the range described above, the disposition of the second light emitting portion 82 and the light receiving portion 83 can be easily implemented. Accordingly, the biological sensor module 8A can be easily manufactured.

The distance L1 between the light emission center C1 of the first light emitting portion 81 and the light reception center CA of the light receiving portion 83 is equal to or greater than the distance L2 between the light emission center C2 of the second light emitting portion 82 and the light reception center CA of the light receiving portion 83, in the −X direction from the first light emitting portion 81 to the light receiving portion 83. According to this, the first light received by the light receiving portion 83 becomes the first light that has reached a part deeper than a reaching part of the second light received by the light receiving portion in the user's body. For that reason, the first light on which the biological information is more reflected can be received by the light receiving portion 83. For example, when the first light is a light having a wavelength of 500 nm or more and less than 600 nm, the first light that has reached more blood vessels is received by the light receiving portion, and thus the first light absorbed according to pulsation can be received by the light receiving portion 83. Therefore, biological information can be detected more accurately.

The distance L2 is 0.5 mm or more and less than 2.0 mm. According to this, in addition to the peak of the noise component contained in the waveform of the second detection signal being clear, the second light emitting portion 82 and the light receiving portion 83 can be easily disposed. Accordingly, the biological sensor module 8A capable of enhancing the detection accuracy of biological information can be easily manufactured.

If the distance L2 is 0.8 mm or more and less than 2.0 mm, the noise component due to the movement of the skin SK can be more effectively removed from the first detection signal, and the second light emitting portion 82 be easily disposed with respect to the light receiving portion 83. Furthermore, if the distance L2 is 0.8 mm or more and 1.5 mm or less, these effects can be more effectively exhibited.

In the light receiving portion 83, the first region 83a having a distance of less than 2.0 mm to the second light emitting portion 82 is larger than the second region 83b having a distance of 2.0 mm or more to the second light emitting portion 82. That is, the area of the first region 83a in a plan view is larger than the area of the second region 83b in a plan view. According to this, the light receiving portion 83 can easily receive the second light emitted from the second light emitting portion 82 and reflected by the epidermis EP and the dermis DE of the user. Accordingly, the signal intensity of the second detection signal can be enhanced, and the noise component can be easily removed from the first detection signal.

The distance LA between the end on the light receiving portion 83 side in the second light emitting portion 82 and the end on the second light emitting portion 82 side in the light receiving portion 83 is 0.01 mm or more and is within 1.00 mm. According to this, the area of the first region 83a in a plan view can be made larger than the area of the second region 83b in a plan view while setting the distance L2 to a value in the range of less than 2.0 mm. Accordingly, the effects described above can be suitably exhibited.

The first light emitting portion 81, the second light emitting portion 82, and the light receiving portion 83 are arranged side by side in the order of the first light emitting portion 81, the second light emitting portion 82, and the light receiving portion 83 along the −X direction which is a predetermined direction in a plan view. In other words, the second light emitting portion 82 is positioned between the first light emitting portion 81 and the light receiving portion 83. According to this, as described above, the path of the second light emitted from the second light emitting portion 82 and reflected by the user's body can be included in the path of the first light emitted from the first light emitting portion 81 and reflected by the user's body. Accordingly, since the movement of the skin SK in the path of the first light can be represented by the second detection signal output from the light receiving portion 83 which receives the second light, the noise component is effectively removed from the first detection signal.

Modification of First Embodiment

In the biological sensor module 8A employed in the biological information measurement device 1, the light receiving portion 83, the second light emitting portion 82, and the first light emitting portion 81 are arranged along the +X direction. However, if the distance between the centers of the light receiving portion 83, the second light emitting portion 82, and the first light emitting portion 81 and the space between the light receiving portion 83 and the second light emitting portion 82 are the same as the distance between centers of the light receiving portion 83, the second light emitting portion 82, and the first light emitting portion 81 and the space between the light receiving portion 83 and the second light emitting portion 82 at the biological sensor module 8A, the layout of the light receiving portion 83, the second light emitting portion 82, and the first light emitting portion 81 can be changed as appropriate. For example, the light receiving portion 83, the second light emitting portion 82, and the first light emitting portion 81 may be arranged along the +Y direction.

In the following description, portions that are the same as or substantially the same as the portions that have already been described will be assigned the same reference numerals and descriptions thereof will be omitted.

First Modification Example of First Embodiment

Figure 10:
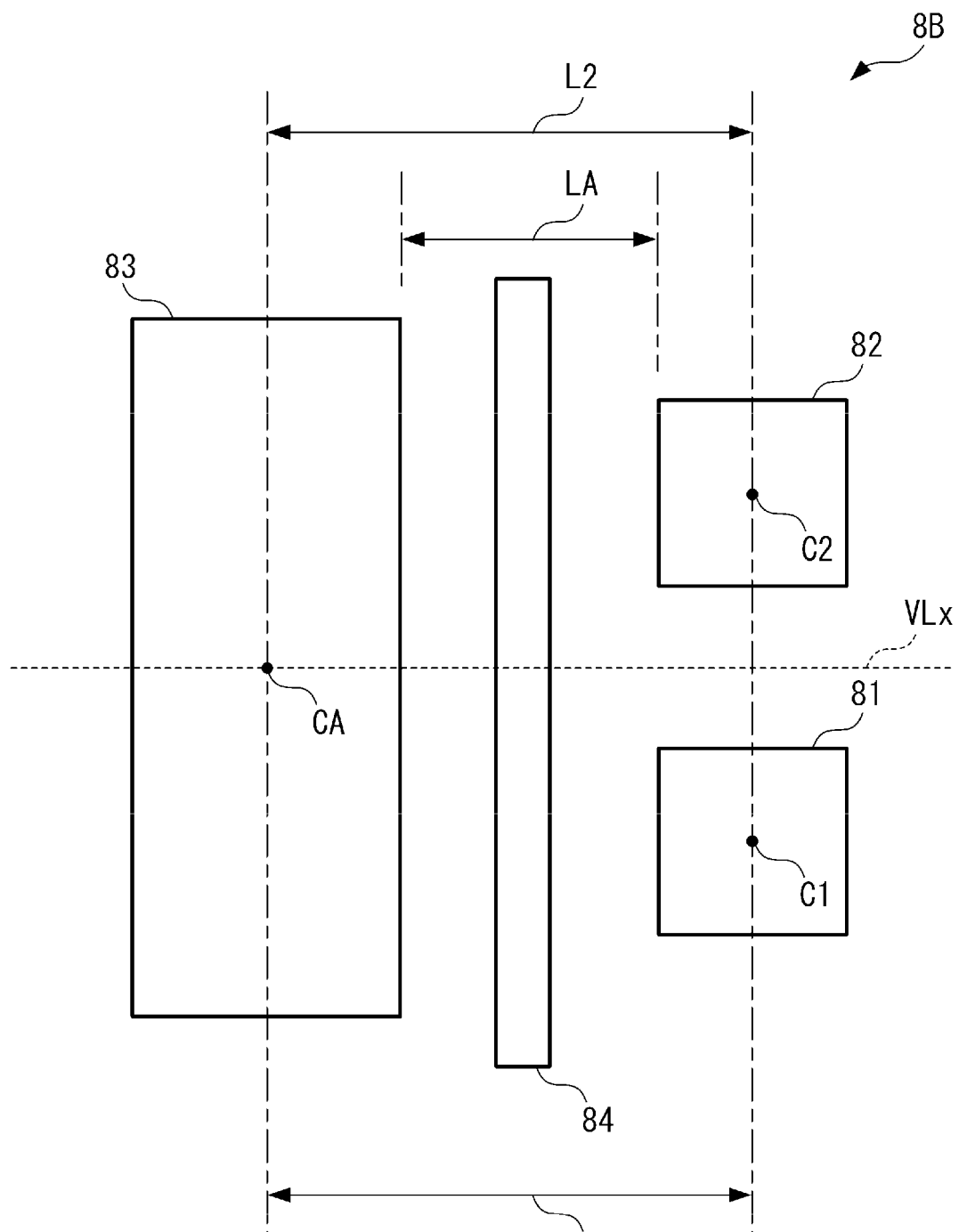
FIG. 10 is a plan view illustrating a modification of the biological sensor module in the first embodiment.

FIG. 10 is a plan view illustrating a biological sensor module 8B which is a modification of the biological sensor module 8A. In FIG. 10, illustration of the substrate 85 is omitted.

For example, the biological sensor module 8B illustrated in FIG. 10 may be employed in the biological information measurement device 1 instead of the biological sensor module 8A.

The biological sensor module 8B has the same configuration and function as the biological sensor module 8A except that the disposition of the first light emitting portion 81 and the second light emitting portion 82 with respect to the light receiving portion 83 is different. That is, the biological sensor module 8B includes the first light emitting portion 81, the second light emitting portion 82, the light receiving portion 83, the light shielding portion 84, and the substrate 85 (not illustrated) for supporting the units.

In the biological sensor module 8B, the first light emitting portion 81 and the second light emitting portion 82 are respectively positioned in the +X direction which is one direction along the short side direction of the light receiving portion 83, with respect to the light receiving portion 83. Further, the second light emitting portion 82 is positioned in the +Y direction with respect to the first light emitting portion 81.

The distance L2 between the light emission center C2 of the second light emitting portion 82 and the light reception center CA of the light receiving portion 83 in the +X direction is set to a value within the range of less than 2.0 mm similarly as in the case of the biological sensor module 8A.

The distance LA between the end on the light receiving portion 83 side in the second light emitting portion 82 and the end on the second light emitting portion 82 side in the light receiving portion 83 in the +X direction is set to a value within the range of 0.01 mm or more and 1.00 mm or less, similarly as in the case of the biological sensor module 8A.

In the biological sensor module 8B, the direction connecting the light emission center C1 of the first light emitting portion 81 and the light emission center C2 of the second light emitting portion 82 is parallel to the +Y direction orthogonal to the +X direction from the light receiving portion 83 toward the first light emitting portion 81 or the second light emitting portion 82. The first light emitting portion 81 and the second light emitting portion 82 are disposed in line symmetry with respect to the virtual line VLx parallel to the +X direction and passing through the light reception center CA. For that reason, the distance L1 between the light emission center C1 of the first light emitting portion 81 and the light reception center CA in the +X direction is the same as the distance L2. However, the present disclosure is not limited thereto, and the distance L1 and the distance L2 may be different. That is, the first light emitting portion 81 may be farther from the light receiving portion 83 than the second light emitting portion 82 in the +X direction. Specifically, the distance L1 is desirably a value within the range of more than 2.0 mm and 5.0 mm or less.

The light shielding portion 84 is disposed between the light receiving portion 83 and the first light emitting portion 81 and the second light emitting portion 82.

Even when such a biological sensor module 8B is employed in the biological information measurement device 1 instead of the biological sensor module 8A, the same effect as described above can be obtained. In addition, in the substrate 85, the dimension in the +X direction of the region where the first light emitting portion 81, the second light emitting portion 82, and the light receiving portion 83 are disposed can be reduced. Accordingly, the biological sensor module 8B can be miniaturized.

Second Modification Example of First Embodiment

Figure 11:
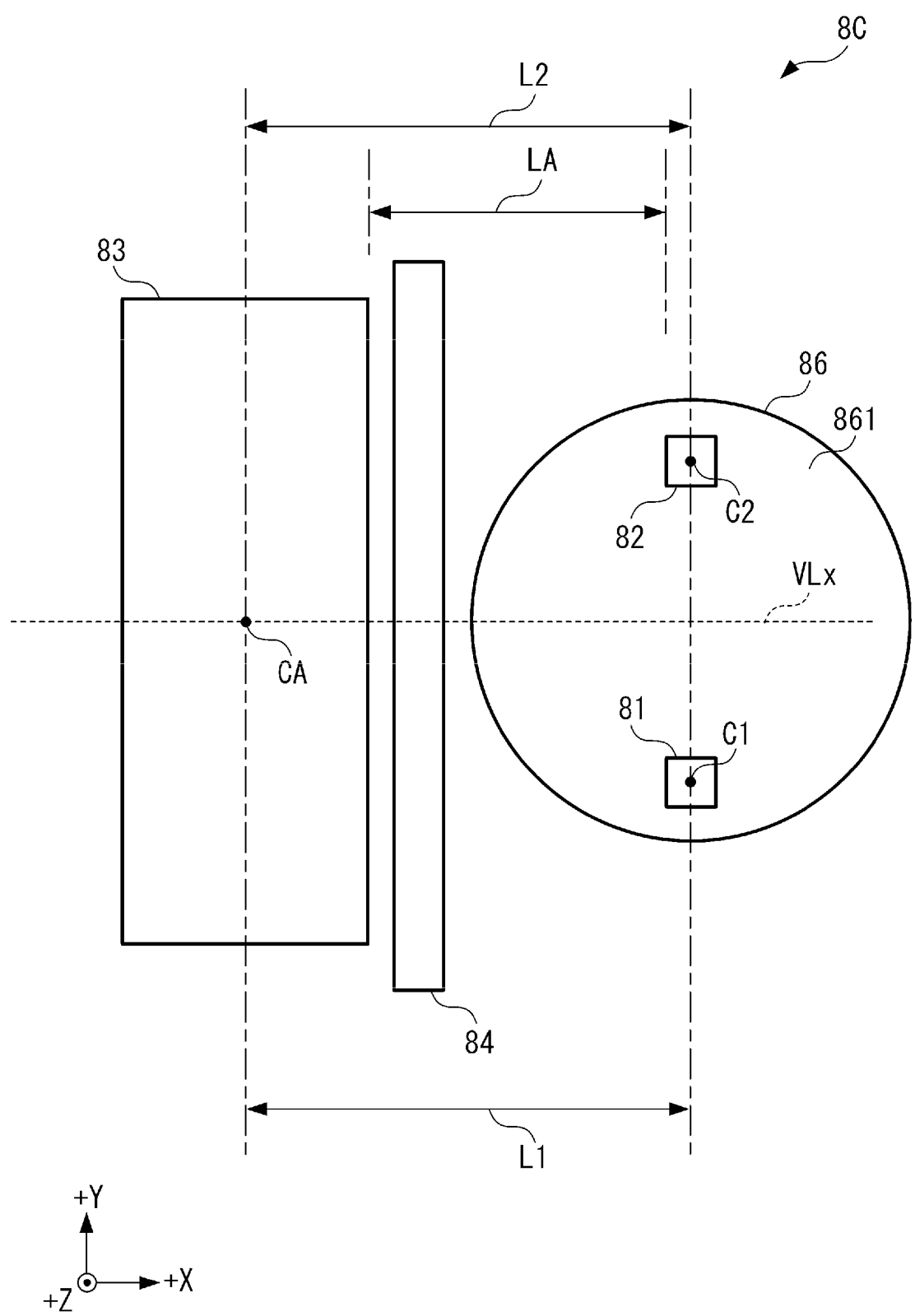
FIG. 11 is a plan view illustrating another modification of the biological sensor module in the first embodiment.

FIG. 11 is a plan view illustrating a biological sensor module 8C which is a modification of the biological sensor module 8A. In FIG. 11, illustration of the substrate 85 is omitted.

Further, for example, the biological sensor module 8C illustrated in FIG. 11 may be employed in the biological information measurement device 1 instead of the biological sensor module 8A.

The biological sensor module 8C has the same configuration and function as the biological sensor module 8B except that the biological sensor module 8C includes a light emitting portion 86 including the first light emitting portion 81 and the second light emitting portion 82.

The light emitting portion 86 is positioned with respect to the light receiving portion 83 in the +X direction which is one direction along the short side direction of the light receiving portion 83. The light emitting portion 86 includes the first light emitting portion 81 positioned on the −Y direction side in the light emitting portion 86, the second light emitting portion 82 positioned on the +Y direction side, and a substrate 861 on which the first light emitting portion 81 and the second light emitting portion 82 are provided.

In the biological sensor module 8C, the distance L2 between the light emission center C2 of the second light emitting portion 82 and the light reception center CA of the light receiving portion 83 in the +X direction is set to a value within the same range as in the case of the biological sensor module 8A. The distance LA between the end on the light receiving portion 83 side in the second light emitting portion 82 and the end on the second light emitting portion 82 side in the light receiving portion 83 in the +X direction is also set to a value within the same range as in the case of the biological sensor module 8A.

In the biological sensor module 8C, similarly to the biological sensor module 8B, the direction connecting the light emission center C1 of the first light emitting portion 81 and the light emission center C2 of the second light emitting portion 82 is parallel to the +Y direction which is the longitudinal direction of the light receiving portion 83. The light emission centers C1 and C2 pass through the light reception center CA of the light receiving portion 83, and are positioned in line symmetry with respect to a virtual line VLx parallel to the +X direction. For that reason, the distance L1 between the light emission center C1 and the light reception center CA in the +X direction is the same as the distance L2. However, the present disclosure is not limited thereto, the distance L1 and the distance L2 may be different. That is, also in the biological sensor module 8C, the first light emitting portion 81 may be farther from the light receiving portion 83 than the second light emitting portion 82 in the +X direction. Specifically, the distance L1 is desirably a value within the range of more than 2.0 mm and 5.0 mm or less.

In addition, the light shielding portion 84 is disposed between the light receiving portion 83 and the light emitting portion 86.

Even when such a biological sensor module 8C is employed in the biological information measurement device 1 instead of the biological sensor module 8A, the same effect as described above can be exhibited.

In addition, since the light emitting portion 86 is configured as one unit in which the first light emitting portion 81 and the second light emitting portion 82 are provided on the substrate 861, the number of parts which constitute the biological sensor module 8C can be reduced, and the process of assembling and manufacturing the biological sensor module 8C can be simplified.

Third Modification Example of First Embodiment

Figure 12:
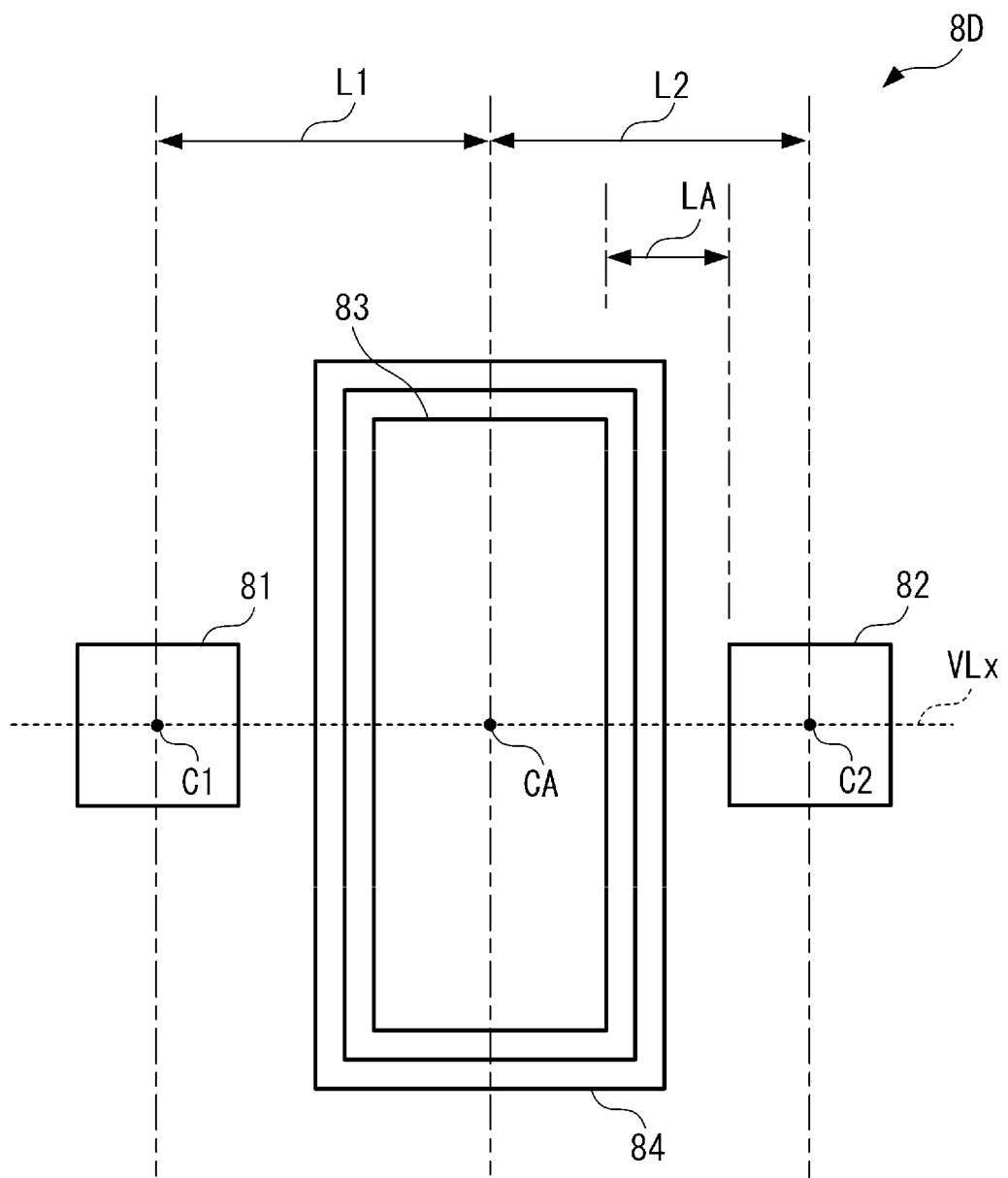
FIG. 12 is a plan view illustrating another modification of the biological sensor module in the first embodiment.

FIG. 12 is a plan view illustrating a biological sensor module 8D which is a modification of the biological sensor module 8A. In FIG. 12, illustration of the substrate 85 is omitted.

Further, for example, the biological sensor module 8D illustrated in FIG. 12 may be employed in the biological information measurement device 1 instead of the biological sensor module 8A.

The biological sensor module 8D has the same configuration and function as the biological sensor module 8A, but the disposition positions of the first light emitting portion 81 and the second light emitting portion 82 are different from those of the biological sensor module 8A.

Specifically, in the biological sensor module 8D, the second light emitting portion 82 is disposed on the opposite side to the first light emitting portion 81 with the light receiving portion 83 interposed therebetween in a plan view. In detail, the first light emitting portion 81 is positioned in the −X direction with respect to the light receiving portion 83, and the second light emitting portion 82 is positioned in the +X direction with respect to the light receiving portion 83. The light emission center C1 of the first light emitting portion 81 and the light emission center C2 of the second light emitting portion 82 are positioned on the virtual line VLx parallel to the +X direction and passing through the light reception center CA.

Also, in the biological sensor module 8D, the distance L2 between the light emission center C2 of the second light emitting portion 82 and the light reception center CA in the +X direction is set to a value within the same range as in the case of the biological sensor module 8A. Further, the distance LA between an end on the light receiving portion 83 side in the second light emitting portion 82 and an end on the second light emitting portion 82 side in the light receiving portion 83 in the +X direction is set to a value within the same range as in the case of the biological sensor module 8A.

In the biological sensor module 8D, the distance L1 between the light emission center C1 of the first light emitting portion 81 and the light reception center CA in the +X direction is longer than the distance L2.

Specifically, the distance L1 is set to a value greater than 2.0 mm and 5.0 mm or less, similarly as in the case of the biological sensor module 8A. This is because, as described above, when the distance L1 is long, the first light emitted from the first light emitting portion 81 travels deep in the user's body, the amount of light absorption by blood increases, and the change in the amount of received light according to the pulsation becomes large. However, the present disclosure is not limited thereto, the distance L1 in the biological sensor module 8D can be changed as appropriate.

In the biological sensor module 8D, in order to shield the first light directed from the first light emitting portion 81 positioned in the −X direction with respect to the light receiving portion 83 to the light receiving portion 83 and the second light directly from the second light emitting portion 82 positioned in the +X direction to the light receiving portion 83, the light shielding portion 84 is formed in a frame shape surrounding the light receiving portion 83 in a plan view.

The same effects as described above can be exhibited even by the biological information measurement device 1 in which such a biological sensor module 8D is employed instead of the biological sensor module 8A.

The first light emitting portion 81, the second light emitting portion 82, and the light receiving portion 83 are disposed along the +X direction which is a predetermined direction in a plan view, and the light receiving portion 83 is positioned between the first light emitting portion 81 and the second light emitting portion 82 in a plan view. According to this, it is possible to easily dispose the first light emitting portion 81 and the second light emitting portion 82 centering on the light receiving portion 83. Furthermore, when the light receiving portion 83 is disposed at the center of the opening 222 provided in the back portion 22 in a plan view, since the first light and the second light reflected by a part pushed by the light-transmitting member 223 can be received by the light receiving portion 83, a more accurate first detection signal can be output.

In the biological sensor module 8D, the first light emitting portion 81 is positioned in the −X direction with respect to the light receiving portion 83, and the second light emitting portion 82 is positioned in the +X direction with respect to the light receiving portion 83. However, the present disclosure is not limited thereto, and when the first light emitting portion 81 and the second light emitting portion 82 are disposed at positions sandwiching the light receiving portion 83, the respective positions of the first light emitting portion 81 and the second light emitting portion 82 with respect to the light receiving portion 83 can be changed as appropriate.

Fourth Modification Example of First Embodiment

Figure 13:
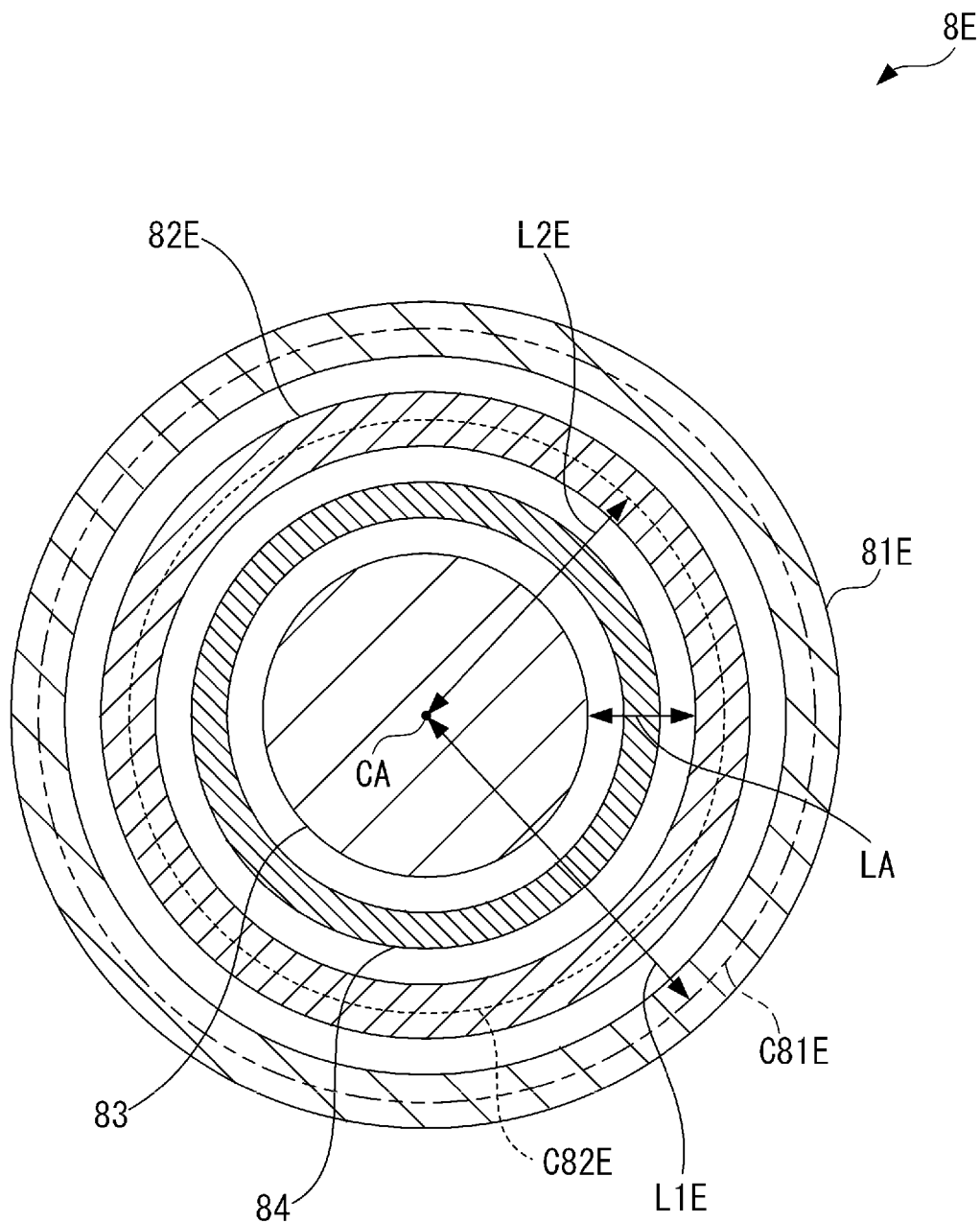
FIG. 13 is a plan view illustrating another modification of the biological sensor module in the first embodiment.

FIG. 13 is a plan view illustrating a biological sensor module 8E which is a modification of the biological sensor module 8A. In FIG. 13, a first light emitting portion 81E, a second light emitting portion 82E, the light receiving portion 83, and the light shielding portion 84 are illustrated by using different hatches in consideration of easy viewing, in addition to illustration of the substrate 85 being omitted.

Further, for example, the biological sensor module 8E illustrated in FIG. 13 may be employed in the biological information measurement device 1 instead of the biological sensor module 8A.

Similar to the biological sensor module 8A, the biological sensor module 8E includes the first light emitting portion 81E, the second light emitting portion 82E, the light receiving portion 83, the light shielding portion 84, and the substrate 85 (not illustrated) for supporting the units, and functions in the same manner as the biological sensor module 8A. In the biological sensor module 8E, the first light emitting portion 81E and the second light emitting portion 82E are provided concentrically around the light reception center CA of the light receiving portion 83.

In the biological sensor module 8E, the light receiving portion 83 is formed in a substantially circular shape in a plan view. As described above, the light reception center CA of the light receiving portion 83 is the center of the light receiving surface 831, which is an active area, in a plan view. The light reception center CA is positioned at the center of the contact portion 221 in a plan view.

In the biological sensor module 8E, the light shielding portion 84 is formed in a substantially circular frame shape surrounding the light receiving portion 83 in a plan view.

The first light emitting portion 81E is provided concentrically around the light reception center CA so as to surround the light receiving portion 83 and the light shielding portion 84 in a plan view, and, emits light having a wavelength of 500 nm or more and less than 600 nm as the first light, similarly to the first light emitting portion 81. That is, the first light emitting portion 81E is configured in annular shape whose center coincides with the light reception center CA. Such a first light emitting portion 81E can exemplify a configuration having annular light emitting region configured by an organic EL element.

The first light emitting portion 81E has a central ring C81E, which is a ring connecting the middle of the outer diameter and the inner diameter of the first light emitting portion 81E and in which the light emitting region is positioned, at a position separated by a distance L1E from the light reception center CA. That is, the distance between the light reception center CA and the central ring C81E, which is the center of the first light emitting portion 81E the radial direction is the distance L1E. The distance L1E is set to a value within the same range as the distance L1.

The second light emitting portion 82E is provided concentrically around the light reception center CA, similarly to the first light emitting portion 81E, and is positioned between the light receiving portion 83, the light shielding portion 84, and the first light emitting portion 81E. That is, the second light emitting portion 82E is configured in annular shape whose center coincides with the light reception center CA, and is positioned between the light shielding portion 84 surrounding the light receiving portion 83 and the first light emitting portion 81E. In other words, the first light emitting portion 81E, the second light emitting portion 82E, and the light receiving portion 83 are arranged side by side, on the inner side of radial direction thereof, in the order of the first light emitting portion 81E, the second light emitting portion 82E, and the light receiving portion 83.

Similar to the second light emitting portion 82, the second light emitting portion 82E emits light having a wavelength of 600 nm or more and 940 nm or less as the second light. Similar to the first light emitting portion 81E, such a second light emitting portion 82E can exemplify a configuration in which a light emitting region configured by an organic EL element is provided in annular shape.

The second light emitting portion 82E has a central ring C82E, which is a ring connecting the middle of the outer diameter and the inner diameter of the second light emitting portion 82E and in which the light emitting region is positioned, at a position separated by a distance L2E from the light reception center CA. That is, the distance between the light reception center CA and the central ring C82E which is the center in the radial direction of the second light emitting portion 82E is the distance L2E. The distance L2E is set to a value within the same range as the distance L2.

Although illustration is omitted, the distance LA between the end on the light receiving portion 83 side in the second light emitting portion 82E and the end on the second light emitting portion 82E side in the light receiving portion 83 in the radial direction is set to a value within the same range as the distance LA in the biological sensor module 8A.

The same effects as described above can be exhibited even by the biological information measurement device 1 in which such a biological sensor module 8E is employed instead of the biological sensor module 8A.

The light receiving portion 83 is surrounded by the first light emitting portion 81E and the second light emitting portion 82E. With this configuration, the light receiving portion 83 can easily receive the first light and the second light. Furthermore, since the first light emitting portion 81E, the second light emitting portion 82E, the light receiving portion 83, and the light shielding portion 84 can be densely disposed, the small-sized biological sensor module 8E can be configured, and also an opening area of the circular opening 222 can be reduced.

Fifth Modification Example of First Embodiment

Figure 14:
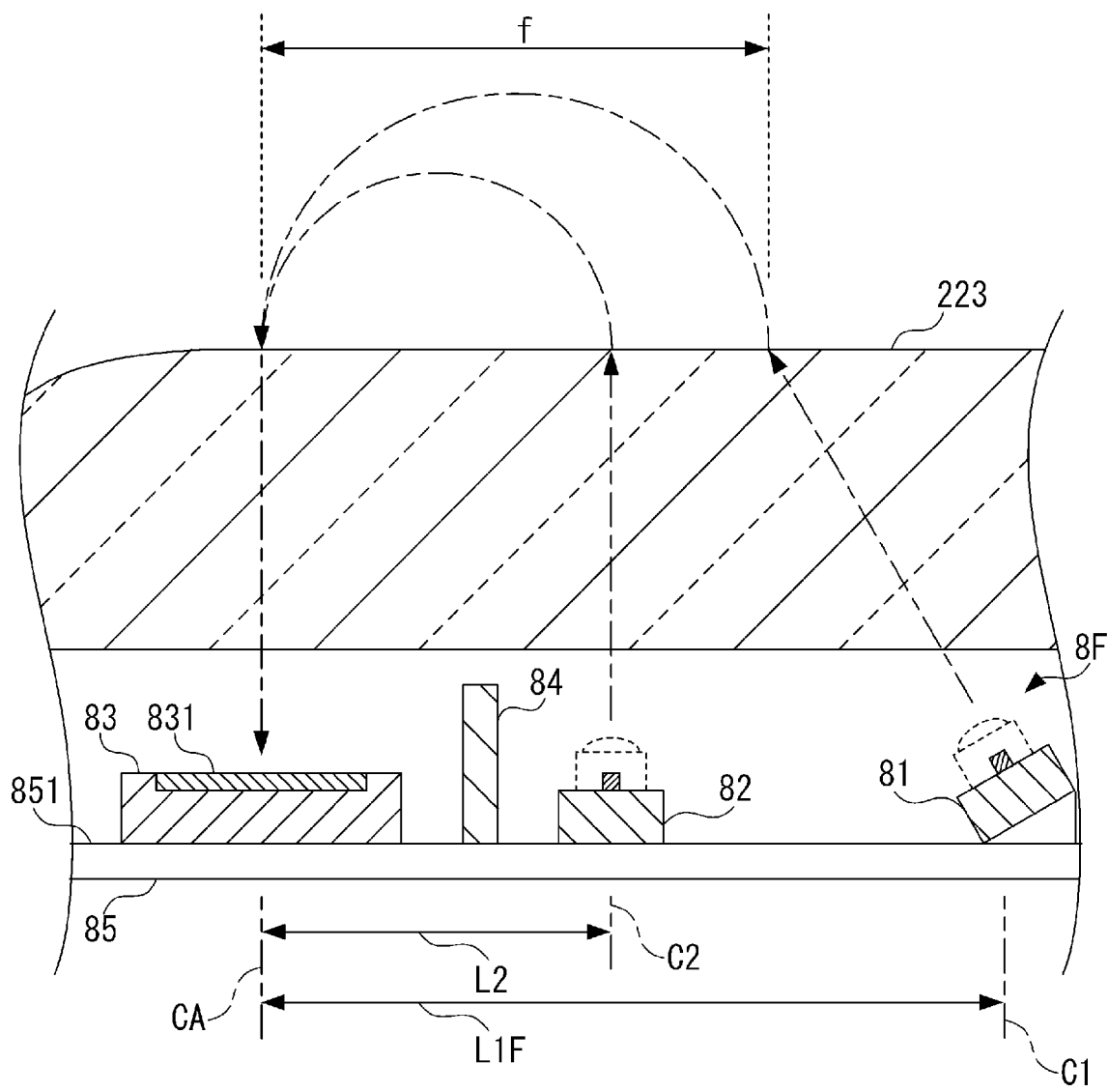
FIG. 14 is a cross-sectional view illustrating another modification of the biological sensor module in the first embodiment.

FIG. 14 is a view illustrating a cross section along the XZ plane of a biological sensor module 8F which is a modification of the biological sensor module 8A.

Further, for example, the biological sensor module 8F illustrated in FIG. 14 may be employed in the biological information measurement device 1 instead of the biological sensor module 8A.

Similar to the biological sensor module 8A, the biological sensor module 8F includes the first light emitting portion 81, the second light emitting portion 82, the light receiving portion 83, the light shielding portion 84, and the substrate 85 (not illustrated) for supporting the units, and functions in the same manner as the biological sensor module 8A. In the biological sensor module 8F, similarly to the biological sensor module 8A, the light emission center C1 of the first light emitting portion 81 and the light emission center C2 of the second light emitting portion 82 are positioned on a virtual line passing through the light reception center CA of the light receiving portion 83 in parallel to the +X direction and the second light emitting portion 82 is disposed between the first light emitting portion 81 and the light receiving portion 83. The distance L2 between the light emission center C2 of the second light emitting portion 82 and the light reception center CA of the light receiving portion 83 in the +X direction is set to a value within the range described above. Although not illustrated, the distance LA between the end on the light receiving portion 83 side in the second light emitting portion 82 and the end on the second light emitting portion 82 side in the light receiving portion 83 in the +X direction is set to a value within the range described above.

Here, in the biological sensor module 8F, the second light emitting portion 82 is disposed such that a traveling direction of a principal ray of the emitted second light is parallel to the +Z direction which is the normal direction of the substrate 85.

On the other hand, the first light emitting portion is disposed such that the traveling direction of the principal ray of the emitted first light intersects the +Z direction. In detail, the first light emitting portion 81 is disposed such that the principal ray of the emitted first light travels in a direction inclined toward the light receiving portion 83 with respect to the +Z direction. With this configuration, the irradiation position of the first light with respect to the epidermis EP (see FIG. 6) of the user can be brought close to the light receiving portion 83 without bringing the first light emitting portion 81 close to the light receiving portion 83. In other words, the first light emitting portion 81 can be disposed at a position away from the light receiving portion 83 and the second light emitting portion 82 while setting a distance f between the irradiation position of the first light from the first light emitting portion 81 on the surface of the epidermis EP and emission position of the first light on the surface of the epidermis EP when the first light reflected by the epidermis EP, the dermis DE and the subcutaneous layer ST is incident on the light receiving portion 83 to a value less than 2.0 mm similarly to the distance d.

As described above, by adjusting the emission direction of the first light from the first light emitting portion 81, even if the distance L1F between the light emission center C1 of the first light emitting portion 81 and the light reception center CA of the light receiving portion 83 in the +X direction is not a value in the same range as the distance L1, the irradiation position of the first light with respect to the surface of the epidermis EP can be adjusted. With this configuration, the path in the user's body of the first light reflected by the user's body and received by the light receiving portion 83 can be adjusted.

The same effects as described above can be exhibited by the biological information measurement device 1 in which such a biological sensor module 8F is employed instead of the biological sensor module 8A.

In addition, since the irradiation position of the first light to the epidermis EP of the user can be adjusted, the first light emitting portion 81 does not necessarily have to be disposed within the range of the distance L1 from the light receiving portion 83. For that reason, the degree of freedom in disposition of the first light emitting portion 81 can be enhanced.

In the biological sensor module 8F, the first light is made to travel in the direction intersecting with the +Z direction by providing the first light emitting portion 81 itself to be inclined with respect to the surface 851 of the substrate 85. However, the present disclosure is not limited thereto, and the first light emitting portion 81 may include an optical path adjusting member which inclines the traveling direction of the first light, which is emitted parallel to the +Z direction, with respect to the +Z direction. A prism can be exemplified as such an optical path adjusting member.

In addition, although the first light emitting portion 81 is disposed so that the emitted first light travels in the direction inclined to the light receiving portion 83 side with respect to the +Z direction, but is not limited thereto. The first light emitting portion 81 may be disposed such that the emitted first light travels in a direction inclined to the opposite side to the light receiving portion 83 with respect to the +Z direction.

Furthermore, instead of or in addition to the first light emitting portion 81, the second light emitting portion 82 may be disposed or configured such that the emitted second light travels in the direction intersecting with the +Z direction. In this case, the irradiation position of the second light can be adjusted in the epidermis EP of the user. Then, in this case, the irradiation position of the second light with respect to the epidermis EP of the user can be brought close to the position according to the light receiving portion 83 without bringing the second light emitting portion 82 itself close to the light receiving portion 83. In other words, even if the distance between the light emission center C2 of the second light emitting portion 82 and the light reception center CA of the light receiving portion 83 is not less than 2.0 mm, the distance between the irradiation position of the second light emitted from the second light emitting portion 82 to the living body and the emission position of light, which enters the living body from the irradiation position and is reflected by the epidermis EP and the dermis DE positioned in a region at a depth of 1.0 mm or less from the surface of the epidermis EP, and is incident on the light receiving portion 83, from the living body can be less than 2.0 mm. For that reason, similarly as in the case of the first embodiment, it is possible to enhance the ratio of the amount of received second light that is reflected by the epidermis EP and the dermis DE of the living body and is received by the light receiving portion 83 among the amounts of light received by the light receiving portion 83. Accordingly, in such a case, the noise component caused by the movement of the skin SK can be effectively removed from the first detection signal similarly to the biological sensor module 8A, and also the degree of freedom in disposition of the second light emitting portion 82 can be enhanced.

Second Embodiment

Next, a second embodiment of the present disclosure will be described. The biological information measurement device according to this embodiment has the same configuration as the biological information measurement device 1 illustrated in the first embodiment, but is different from the biological information measurement device 1 in that a plurality of first light emitting portions and a plurality of second light emitting portions are provided. In the following description, portions that are the same as or substantially the same as the portions already described will be given the same reference numerals and descriptions thereof will be omitted.

Figure 15:
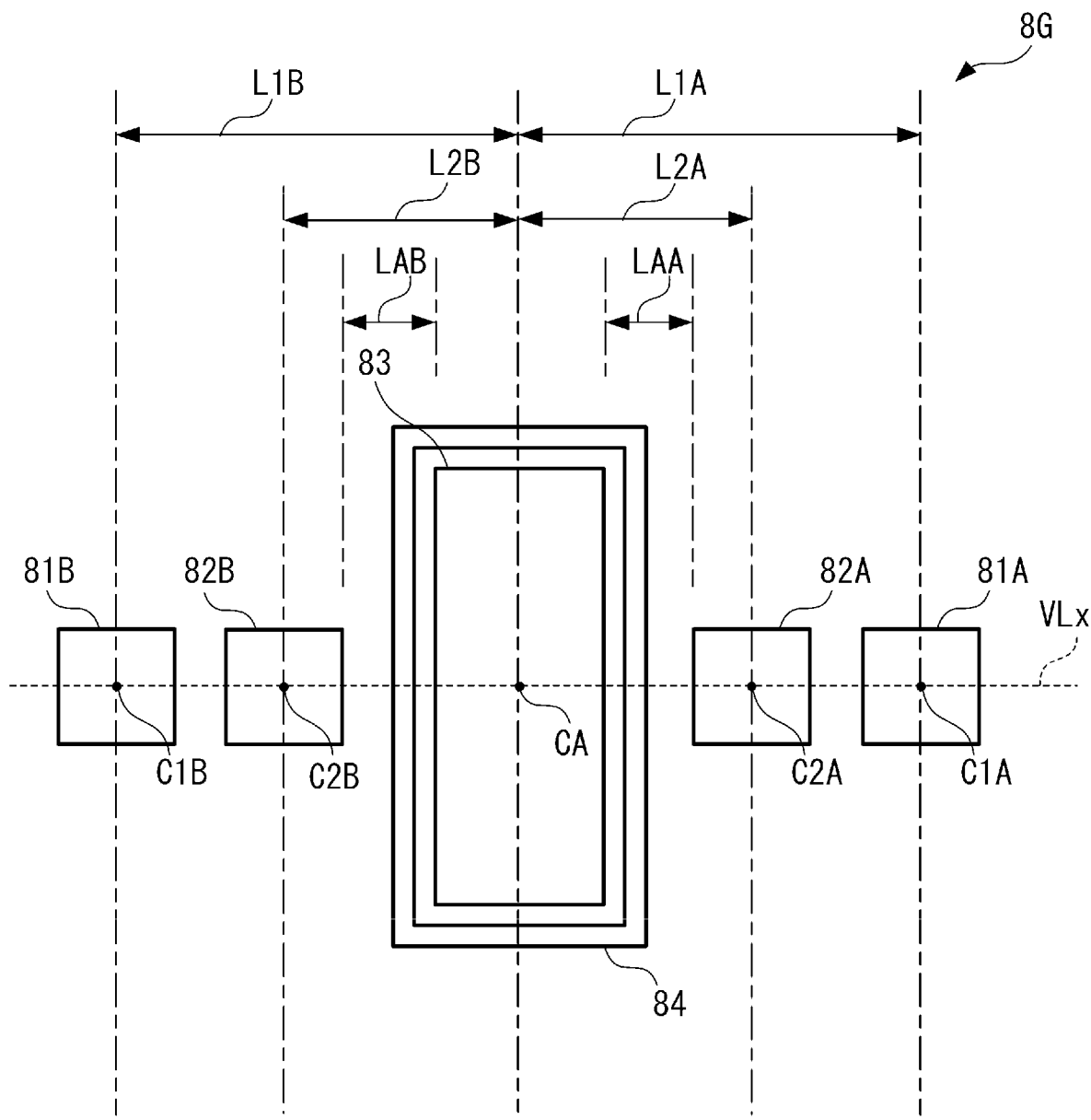
FIG. 15 is a plan view illustrating a biological sensor module provided in a biological information measurement device according to a second embodiment of the present disclosure.

FIG. 15 is a plan view illustrating a biological sensor module 8G included in the biological information measurement device according to this embodiment. In FIG. 15, the substrate 85 is not illustrated.

The biological information measurement device according to this embodiment has the same configuration and function as the biological information measurement device 1 except that the biological information measurement device includes the biological sensor module 8G instead of the biological sensor module 8A. In addition, as illustrated in FIG. 15, the biological sensor module 8G includes two first light emitting portions 81A and 81B, two second light emitting portions 82A and 82B, one light receiving portion 83, and one light shielding portion 84, and the substrate 85 (not illustrated) for supporting the units, and functions in the same manner as the biological sensor module 8A.

Each of the first light emitting portions 81A and 81B has the same configuration as the first light emitting portion 81, and emits light of a wavelength of 500 nm or more and less than 600 nm as the first light. The first light emitting portions 81A and 81B are provided at positions sandwiching the second light emitting portions 82A and 82B and the light receiving portion 83 in the +X direction. The light emission center C1A of the first light emitting portion 81A and the light emission center C1B of the first light emitting portion 81B are positioned on the virtual line VLx parallel to the +X direction and passing through the light reception center CA.

The first light emitting portion 81A is disposed in the +X direction with respect to the light receiving portion 83. A distance L1A between a light emission center C1A of the first light emitting portion 81A and the light reception center CA in the +X direction is a value within a range set for the distance L1.

The first light emitting portion 81B is disposed in the −X direction with respect to the light receiving portion 83. A distance L1B between a light emission center C1B of the first light emitting portion 81B and the light reception center CA in the +X direction is also a value within the range set for the distance L1.

The distance L1A and the distance L1B may be different.

Each of the second light emitting portions 82A and 82B has the same configuration as the second light emitting portion 82, and emits light having a wavelength of 600 nm or more as the second light. The second light emitting portions 82A and 82B are provided at positions sandwiching the light receiving portion 83 in the +X direction. In other words, the second light emitting portions 82A and 82B are provided at positions sandwiched between the first light emitting portions 81A and 81B in the +X direction, the second light emitting portion 82A is positioned between the light receiving portion 83 and the first light emitting portion 81A, and the second light emitting portion 82B is positioned between the light receiving portion 83 and the first light emitting portion 81B. The second light emitting portion 82A is positioned in the +X direction with respect to the light receiving portion 83, and the second light emitting portion 82B is positioned in the −X direction with respect to the light receiving portion 83.

A light emission center C2A of the second light emitting portion 82A and a light emission center C2B of the second light emitting portion 82B are positioned on the virtual line VLx.

A distance L2A between the light emission center C2A of the second light emitting portion 82A and the light reception center CA in the +X direction is set to a value within the same range as the distance L2. A distance LAA between the end on the light receiving portion 83 side in the second light emitting portion 82A and the end on the second light emitting portion 82A in the light receiving portion 83 in the +X direction is set to a value within the same range as the distance LA.

The distance L2B between the light emission center C2B of the second light emitting portion 82B and the light reception center CA in the +X direction is set to a value within the same range as the distance L2. Further, a distance LAB between the end on the light receiving portion 83 side in the second light emitting portion 82B and the end on the second light emitting portion 82B in the light receiving portion 83 in the +X direction is set to a value within the same range as the distance LA.

The distances L2A and L2B may be different. Similarly, the distances LAA and LAB may be different.

Effect of Second Embodiment

The biological information measurement device including the biological sensor module 8G according to this embodiment described above can exhibit the same effect as the biological information measurement device 1 including the biological sensor module 8A illustrated in the first embodiment.

Besides, in the biological sensor module 8G, the two second light emitting portions 82A and 82B sandwich the light receiving portion 83 in a plan view, and the two first light emitting portions 81A and 81B sandwich the second light emitting portions 82A and 82B and the light receiving portion 83 in a plan view. With this configuration, the following effects can be exhibited.

That is, in the biological sensor module 8G, when a pulse wave which is one of the biological information is detected, at least one of the first light emitting portions 81A and 81B is turned on. When each of the first light emitting portions 81A and 81B is turned on, the amount of received first light received by the light receiving portion 83 can be increased. The first light emitting portions 81A and 81B are individually turned on, and it is also possible to use a first light emitting portion suitable for pulse wave detection among the first light emitting portions 81A and 81B, based on the respective waveforms of the first detection signal output from the light receiving portion 83 when the first light emitting portion 81A is turned on and the first detection signal output from the light receiving portion 83 when the first light emitting portion 81B is turned on.

Similarly, when each of the second light emitting portions 82A and 82B is turned on, the amount of received second light received by the light receiving portion 83 can be increased. The second light emitting portions 82A and 82B are individually turned on, and it is also possible to use a second light emitting portion suitable for noise component detection among the second light emitting portions 82A and 82B, based on the respective waveforms of the second detection signal output from the light receiving portion 83 when the second light emitting portion 82A is turned on and the second detection signal output from the light receiving portion 83 when the second light emitting portion 82B is turned on.

Modification of Second Embodiment

The biological sensor module 8G includes the second light emitting portions 82A and 82B sandwiching the light receiving portion 83 in the +X direction, and first light emitting portions 81A and 81B sandwiching the second light emitting portions 82A and 82B and the light receiving portion 83 in the +X direction. However, the present disclosure is not limited thereto, and the second light emitting portions 82A and 82B may be disposed at the positions sandwiching the light receiving portion 83 in the +Y direction, and the first light emitting portions 81A and 81B may be disposed at the positions sandwiching the second light emitting portions 82A and 82B and the light receiving portion 83 in the +Y direction. That is, an extending direction of the virtual line passing through the light reception center CA and intersecting the light emission centers C1A, C2A, C2B, and C1B is not limited to the direction parallel to the +X direction, and may be another direction.

Figure 16:
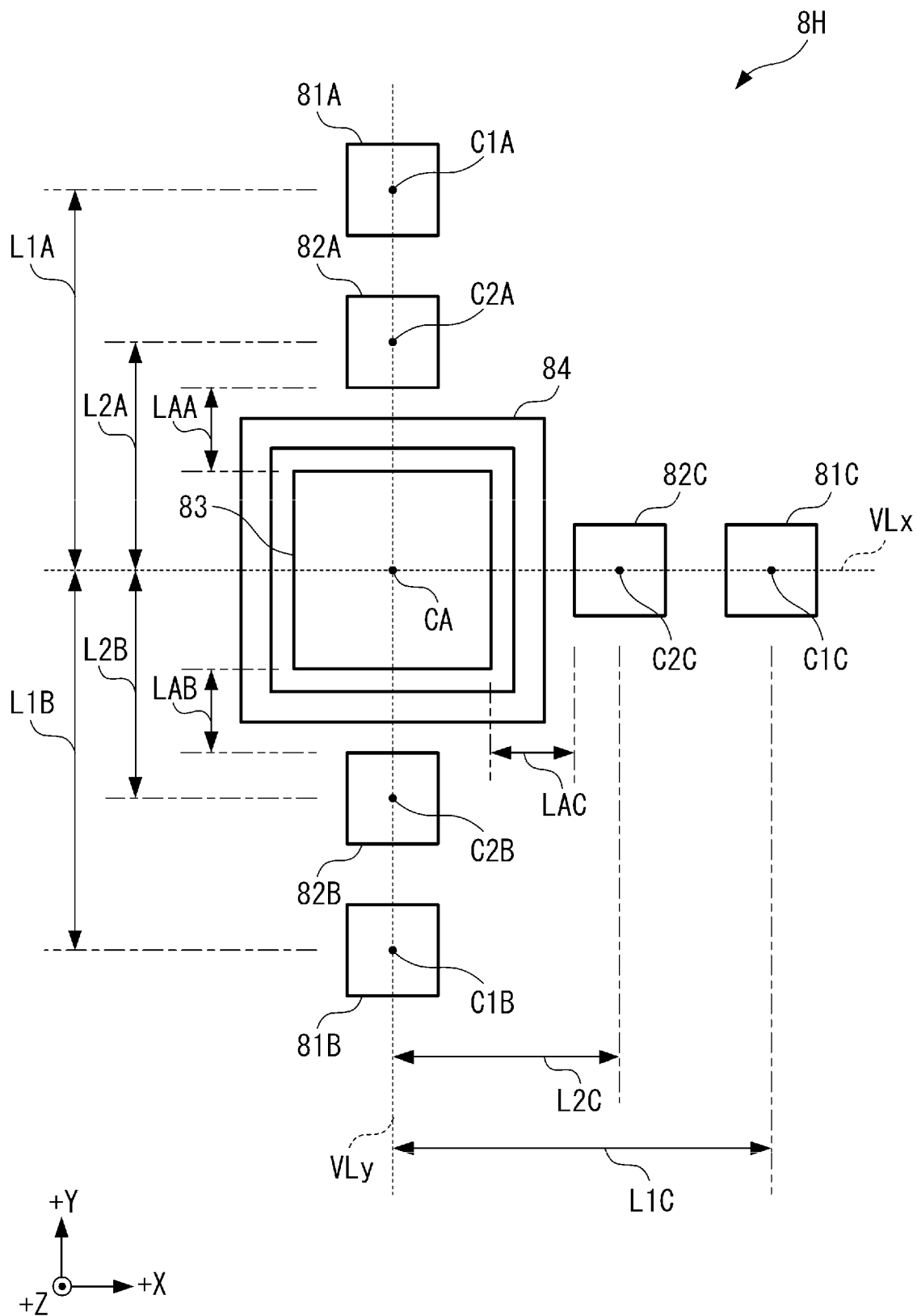
FIG. 16 is a plan view illustrating a modification of the biological sensor module in the second embodiment.

FIG. 16 is a plan view illustrating a biological sensor module 8H which is a modification of the biological sensor module 8G. In FIG. 16, illustration of the substrate 85 is omitted.

For example, the biological sensor module 8H illustrated in FIG. 16 may be employed instead of the biological sensor module 8G.

The biological sensor module 8H includes three first light emitting portions 81A, 81B, and 81C, three second light emitting portions 82A, 82B, and 82C, one light receiving portion 83, and one light shielding portion 84, and the substrate 85 (not illustrated) for supporting the units, and functions in the same manner as the biological sensor module 8G. The light receiving portion 83 and the light shielding portion 84 are disposed in the same manner as the biological sensor module 8G. For example, the light reception center CA of the light receiving portion 83 is positioned at the center of the contact portion 221 in a plan view.

Each of the three first light emitting portions 81A, 81B, and 81C has the same configuration as that of the first light emitting portion 81, and emits light having a wavelength of 500 nm or more and less than 600 nm as the first light. The first light emitting portions 81A, 81B, and 81C are provided outside the second light emitting portions 82A, 82B, and 82C, the light receiving portion 83, and the light shielding portion 84.

Specifically, the first light emitting portions 81A and 81B are disposed at positions sandwiching the second light emitting portions 82A and 82B, the light receiving portion 83, and the light shielding portion 84 in the +Y direction. The first light emitting portion 81C is disposed at a position sandwiching the second light emitting portion 82C with the light receiving portion 83 in the +X direction. That is, the light emission center C1A of the first light emitting portion 81A and the light emission center C1B of the first light emitting portion 81B are positioned on a virtual line VLy parallel to the +Y direction and passing through the light reception center CA, and a light emission center C1C of the first light emitting portion 81C is positioned on the virtual line VLx parallel to the +X direction and passing through the light reception center CA.

The first light emitting portion 81A is disposed in the +Y direction with respect to the light receiving portion 83, the first light emitting portion 81B is disposed in the −Y direction with respect to the light receiving portion 83, and the first light emitting portion 81C is disposed in the +X direction with respect to the light receiving portion 83. Each of the distance L1A between the light emission center C1A of the first light emitting portion 81A and the light reception center CA in the +Y direction, the distance L1B between the light emission center C2B of the first light emitting portion 81B and the light reception center CA in the +Y direction, and the distance L1C between the light emission center C1C of the first light emitting portion 81C and the light reception center CA in the +X direction is a value within the range set for the distance L1.

The distances L1A, L1B, and L1C may be values different from each other as long as the distances are values within the range described above.

Each of three second light emitting portions 82A, 82B, and 82C has the same configuration as that of the second light emitting portion 82, and emits light having a wavelength of 600 nm or more as the second light. The second light emitting portions 82A, 82B, and 82C surround the light receiving portion 83 and the light shielding portion 84, and are disposed at positions surrounded by the first light emitting portions 81A, 81B, and 81C.

Specifically, the second light emitting portions 82A and 82B sandwich the light receiving portion 83 and the light shielding portion 84 in the +Y direction, and are disposed at positions sandwiched by the first light emitting portions 81A and 81B. The second light emitting portion 82C is disposed in the +X direction with respect to the light receiving portion 83 and the light shielding portion 84, and is disposed at a position sandwiched by the light shielding portion 84 surrounding the light receiving portion 83 and the first light emitting portion 81C. That is, the light emission center C2A of the second light emitting portion 82A and the light emission center C2B of the second light emitting portion 82B are positioned on the virtual line VLy, and the light emission center C2C of the second light emitting portion 82C is positioned on the virtual line VLx.

Each of the distance L2A between the light emission center C2A of the second light emitting portion 82A and the light reception center CA in the +Y direction, the distance L2B between the light emission center C2B of the second light emitting portion 82B and the light reception center CA in the +Y direction, and the distance L2C between the light emission center C2C of the second light emitting portion 82C and the light reception center CA in the +X direction is set to a value within the range set for the distance L2.

Each of the distance LAA between the end on the light receiving portion 83 side in the second light emitting portion 82A and the end on the second light emitting portion 82A side in the light receiving portion 83 in the +Y direction, the distance LAB between the end on the light receiving portion 83 side in the second light emitting portion 82B and the end on the second light emitting portion 82B side in the light receiving portion 83 in the +Y direction, and a distance LAC between the end on the light receiving portion 83 side in the second light emitting portion 82C and the end on the second light emitting portion 82C side in the light receiving portion 83 in the +X direction is set to a value within the range set for the distance LA.

The distances L2A, L2B, and L2C may be values different from each other as long as the distances are values within the range described above. Similarly, the distances LAA, LAB, and LAC may be values different from each other as long as the distances are within the range described above.

The same effect as the biological information measurement device including the biological sensor module 8G can be exhibited even by the biological information measurement device including such a biological sensor module 8H.

Third Embodiment

Next, a third embodiment of the present disclosure will be described.

The biological information measurement device according to this embodiment has the same configuration as the biological information measurement device 1, but differs from the biological information measurement device 1 in that a plurality of light receiving portions are provided. In the following description, portions that are the same as or substantially the same as the portions described above are given the same reference numerals and descriptions thereof will be omitted.

Figure 17:
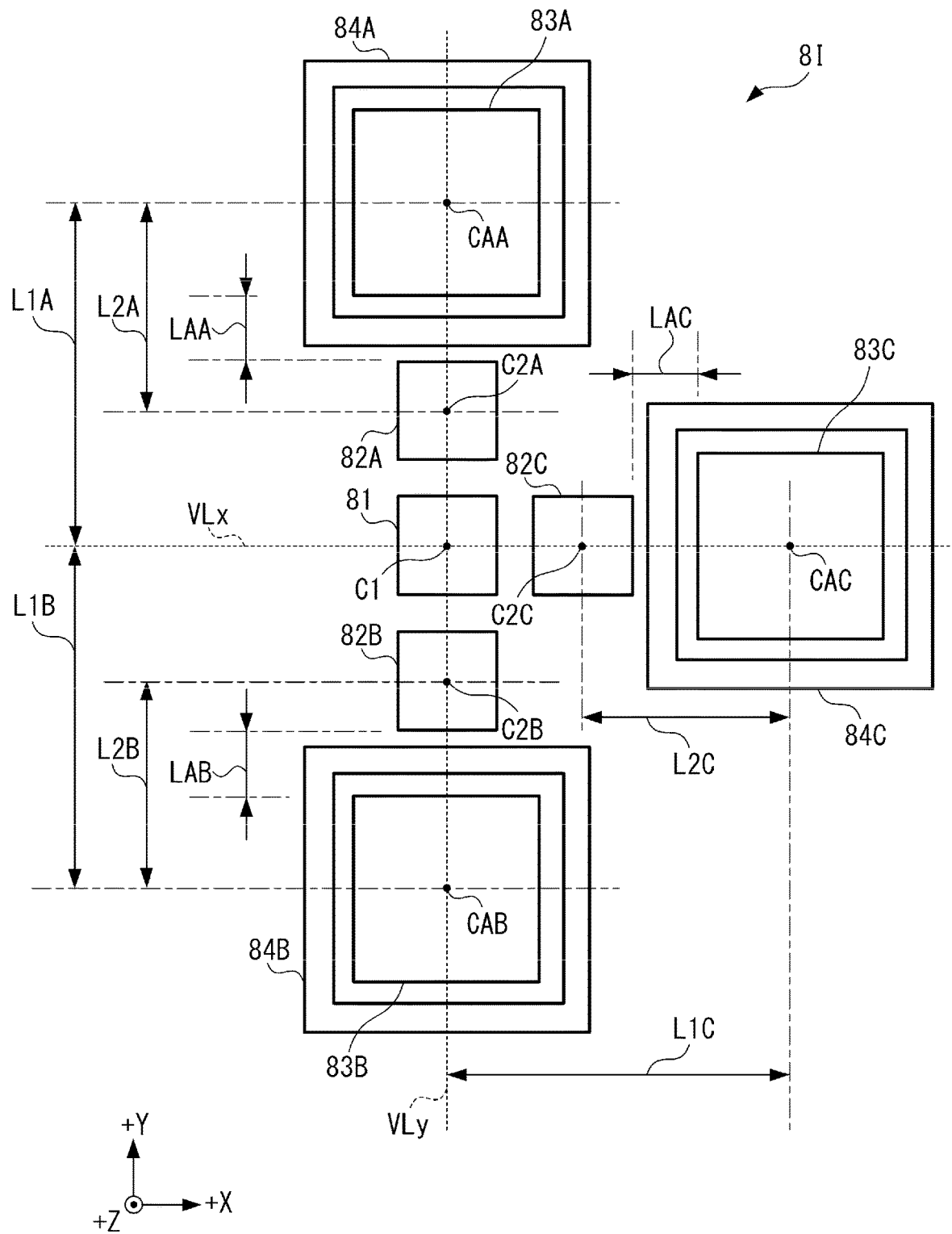
FIG. 17 is a plan view illustrating a biological sensor module included in a biological information measurement device according to a third embodiment of the present disclosure.

FIG. 17 is a plan view illustrating a biological sensor module 8I included in the biological information measurement device according to this embodiment. In FIG. 17, illustration of the substrate 85 is omitted.

The biological information measurement device according to this embodiment has the same configuration and function as the biological information measurement device 1 except that the biological information measurement device includes the biological sensor module 8I instead of the biological sensor module 8A. As illustrated in FIG. 17, the biological sensor module 8I includes one first light emitting portion 81, three second light emitting portions 82A, 82B, and 82C, three light receiving portions 83A, 83B, and 83C, and three light shielding portions 84A and 84B, and 84C, and the substrate 85 (not illustrated) supporting the units, and functions in the same manner as the biological sensor module 8A.

As described above, the first light emitting portion 81 emits light having a wavelength of 500 nm or more and less than 600 nm as the first light. In the biological sensor module 8I, the first light emitting portion 81 is positioned substantially at the center of the region where the second light emitting portions 82A, 82B, and 82C, the light receiving portions 83A, 83B, and 83C, and the light shielding portions 84A, 84B, and 84C are disposed in a plan view.

In the biological sensor module 8I, the light emission center C1 of the first light emitting portion 81 is positioned at the center of the contact portion 221 in a plan view. The first light emitting portion 81 has a substantially square shape in a plan view, but is not limited thereto. For example, the first light emitting portion 81 may have a substantially circular shape in a plan view or a rectangular shape in a plan view.

The second light emitting portions 82A, 82B, and 82C are positioned in the +Y direction, the −Y direction, and the +X direction, respectively, with respect to the first light emitting portion 81. In other words, the second light emitting portion 82A is disposed between the first light emitting portion 81 and the light receiving portion 83A in the +Y direction, the second light emitting portion 82B is disposed between the first light emitting portion 81 and the light receiving portion 83B in the +Y direction, and the second light emitting portion 82C is disposed between the first light emitting portion 81 and the light receiving portion 83C in the +X direction.

Each of the second light emitting portions 82A, 82B, and 82C has the same configuration as that of the second light emitting portion 82, and emits light having a wavelength of 600 nm or more as the second light.

Each of the light receiving portions 83A, 83B and 83C has the same configuration as the light receiving portion 83. The light receiving portion 83A is positioned in the +Y direction with respect to the second light emitting portion 82A, the light receiving portion 83B is positioned in the −Y direction with respect to the second light emitting portion 82B, and the light receiving portion 83C positioned in the +X direction with respect to the second light emitting portion 82C. That is, the light receiving portions 83A and 83B are disposed at positions sandwiching the first light emitting portion 81 and the second light emitting portions 82A and 82B in the +Y direction. In detail, the light receiving portion 83A is disposed at a position sandwiching the second light emitting portion 82A with the first light emitting portion 81 in the +Y direction, and the light receiving portion 83B is disposed at a position sandwiching the second light emitting portion 82B with the first light emitting portion 81 in the +Y direction. The light receiving portion 83C is disposed at a position sandwiching the second light emitting portion 82C between the light receiving portion 83C and the first light emitting portion 81 in the +X direction.

Each of the light receiving portions 83A, 83B, and 83C receives the first light emitted from the first light emitting portion 81 and reflected by the epidermis EP, dermis DE, and subcutaneous layer ST of the user. The light receiving portion 83A receives the second light emitted from the second light emitting portion 82A and reflected by the epidermis EP and the dermis DE of the user. Similarly, the light receiving portion 83B receives the second light emitted from the second light emitting portion 82B and reflected by the epidermis EP and the dermis DE of the user, and the light receiving portion 83C receives the second light emitted from the second light emitting portion 82C and reflected by the epidermis EP and the dermis DE of the user.

The light shielding portions 84A, 84B, and 84C are provided in accordance with the corresponding light receiving portion among the light receiving portions 83A, 83B, and 83C. Specifically, the light shielding portion 84A is provided in a frame shape surrounding the light receiving portion 83A in a plan view. That is, the light shielding portion 84A is provided between the first light emitting portion 81, and the second light emitting portion 82A and the light receiving portion 83A. The same applies to the light shielding portion 84B provided in a frame shape according to the light receiving portion 83B and the light shielding portion 84C provided in a frame shape according to the light receiving portion 83C.

Here, each of a light reception center CAA of light receiving portion 83A, the light emission center C2A of second light emitting portion 82A, the light emission center C1 of first light emitting portion 81, the light emission center C2B of second light emitting portion 82B, and a light reception center CAB of the light receiving portion 83B is positioned on the virtual line VLy parallel to the +Y direction.

Each of the light emission center C1 of the first light emitting portion 81, the light emission center C2C of the second light emitting portion 82C, and the light reception center CAC of the light receiving portion 83C is positioned on the virtual line VLx parallel to the +X direction.

The virtual line VLy and the virtual line VLx intersect at the light emission center C1.

Each of the distance L1A between the light emission center C1 and the light reception center CAA in the +Y direction, the distance L1B between the light emission center C1 and the light reception center CAB in the +Y direction, and the distance L1C between the light emission center C1 and the light reception center CAC in the +X direction is set to a value within a range set according to the distance L1.

The distances L1A, L1B, and L1C may be values different from each other as long as the distances are values within the range described above.

Each of the distance L2A between the light emission center C2A and the light reception center CAA in the +Y direction, the distance L2B between the light emission center C2B and the light reception center CAB in the +Y direction, and the distance L2C between the light emission center C2C and the light reception center CAC in the +X direction is set to a value within a range set according to the distance L2.

Each of the distance LAA between the end on the light receiving portion 83A side in the second light emitting portion 82A and the end on the second light emitting portion 82A side in the light receiving portion 83A in the +Y direction, the distance LAB between the end on the light receiving portion 83B side in the second light emitting portion 82B and the end on the second light emitting portion 82B side in the light receiving portion 83B side in the +Y direction, and the distance LAC between the end on the light receiving portion 83C side in the second light emitting portion 82C and the end on the second light emitting portion 82C side in the light receiving portion 83C in the +X direction is set to a value within a range set according to the distance LA.

The distances L2A, L2B, and L2C may be different from each other as long as the distances are values within the range described above. Similarly, the distances LAA, LAB, and LAC may be values different from each other as long as the distances are within the range described above.

The biological information measurement device including such a biological sensor module 8I can exhibit the same effect as the biological information measurement device 1 including the biological sensor module 8A.

Fourth Embodiment

Next, a fourth embodiment of the present disclosure will be described. The biological information measurement device according to this embodiment has the same configuration as the biological information measurement device illustrated in the third embodiment. However, the biological information measurement device according to this embodiment differs from the biological information measurement device illustrated in the third embodiment in that the biological information measurement device according to this embodiment includes a light emitting element that emits light of a wavelength different from that of the first light and the second light, in addition to the light emitting element in which the first light emitting portion emits the first light. In the following description, portions that are the same as or substantially the same as the portions already described are given the same reference numerals and descriptions thereof will be omitted.

Figure 18:
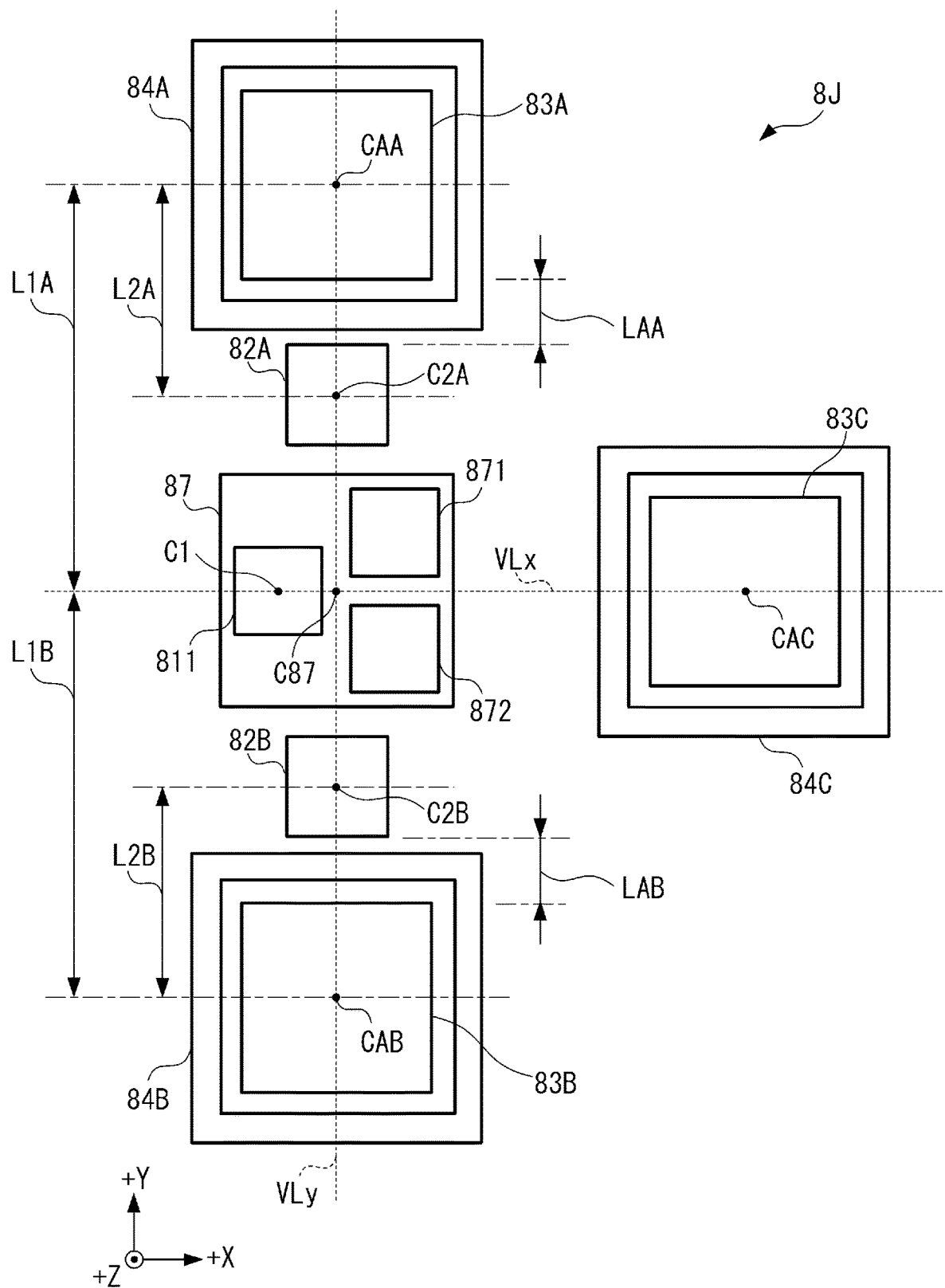
FIG. 18 is a plan view illustrating a biological sensor module provided in a biological information measurement device according to a fourth embodiment of the present disclosure.

FIG. 18 is a plan view illustrating a biological sensor module 8J included in the biological information measurement device according to this embodiment. In FIG. 18, the substrate 85 is not illustrated.

The biological information measurement device according to this embodiment has the same configuration and function as the biological information measurement device illustrated in the third embodiment, except that the biological information measurement device according to this embodiment includes the biological sensor module 8J instead of the biological sensor module 8I.

As illustrated in FIG. 18, the biological sensor module 8J has the same configuration and function as those of the biological sensor module 8I except that the biological sensor module 8J includes a first light emitting portion 87 instead of the first light emitting portion 81 but does not include the second light emitting portion 82C. That is, the biological sensor module 8J includes the first light emitting portion 87, the second light emitting portions 82A and 82B, the light receiving portions 83A, 83B, and 83C, the light shielding portions 84A, 84B, and 84C, and the substrate 85 (not illustrated) for supporting the units.

The second light emitting portion 82A is disposed between the first light emitting portion 87 and the light receiving portion 83A in the +Y direction, and the second light emitting portion 82B is disposed between the first light emitting portion 87 and the light receiving portion 83B in the +Y direction.

The first light emitting portion 87 includes a light emitting element 811 which emits a light having a wavelength of 500 nm or more and less than 600 nm as the first light and two light emitting elements 871 and 872 that emit light having wavelengths different from the first light and the second light. The light emitting element 811 is positioned on the −X direction side with respect to the center C87 of the first light emitting portion 87 in a plan view, and the light emitting elements 871 and 872 are positioned on the +X direction with respect to the center C87.

The light emission center C1 of the light emitting element 811, that is, the light emission center C1 of the first light in the first light emitting portion 87 is positioned on an virtual line VLx parallel to the +X direction. The distance L1A between the light emission center C1 and the light reception center CAA in the +Y direction and the distance L1B between the light emission center C1 and the light reception center CAB in the +Y direction are set to the values within the range set for the distance L1.

The first light emitted from the light emitting element 811 and reflected by the user's body is received by the light receiving portions 83A and 83B. The light emission center C1 of the light emitting element 811 is deviated from the virtual line VLy in the −X direction, but is not limited thereto. The light emission center C1 may be positioned on the virtual line VLy. In this case, the path of the second light emitted from the second light emitting portions 82A and 82B, reflected by the skin SK of the user, and incident on the light receiving portions 83A and 83B can be included in the path of the first light emitted from the light emitting element 811 and reflected by the body of the user, and incident on the light receiving portions 83A and 83B.

The light emitting elements 871 and 872 are used when detecting and measuring biological information different from the biological information detected and measured based on the first detection signal according to the amount of received first light. The light emitting elements 871 and 872 respectively emit third light and fourth light having different wavelengths from the first light and the second light and having wavelengths different from each other.

In this embodiment, the light emitting elements 871 and 872 are used when detecting SpO2 (percutaneous arterial blood oxygen saturation) which is one of biological information. One of the light emitting elements 871 and 872 emits light having a wavelength of less than 805 nm as the third light, and the other emits light having a wavelength of 805 nm or more as the fourth light. For example, the light emitting element 871 emits light of 665 nm as the third light, and the light emitting element 872 emits light of 880 nm as the fourth light.

The third light and the fourth light emitted from the light emitting elements 871 and 872 and passed through the user's body are received by the light receiving portion 83C. The light receiving portion 83C outputs a third detection signal according to the amount of received third light and a fourth detection signal according to the amount of received fourth light. Then, the processing unit 7 uses the third detection signal as a reference signal for noise removal, and calculates SpO2 based on the fourth detection signal from which the noise component has been removed using the third detection signal.

Even in such a biological sensor module 8J, the distance L2A between the light emission center C2A and the light reception center CAA in the +Y direction and the distance L2B between the light emission center C2B and the light reception center CAB in the +Y direction are set to values within the range set for the distance L2. The distance LAA between an end on the light receiving portion 83A side in the second light emitting portion 82A and an end on the second light emitting portion 82A side in the light receiving portion 83A in the +Y direction, and the distance LAB between the end on the light receiving portion 83B side in the second light emitting portion 82B and the end on the second light emitting portion 82B side in the light receiving portion 83B in the +Y direction are set to values within the range set for the distance LA.

The distances L2A and L2B may be different values as long as the distances L2A and L2B are within the range described above, and the distances LAA and LAB may also be different values as long as the distances LAA and LAB are within the range described above.

A biological information measurement device including such a biological sensor module 8J can exhibit the same effects as the biological information measurement device including the biological sensor module 8I described above, and can also exhibit the following effects.

The first light emitting portion 87 includes light emitting elements 871 and 872 for emitting the third light and the fourth light, in addition to the light emitting element 811 for emitting the first light. The third light and the fourth light having passed through the user's body are respectively received by the light receiving portion 83C, and a third detection signal according to the amount of received third light and a fourth detection signal according to the amount of received fourth light are output from the light receiving portion 83C. Then, the processing unit 7 calculates, for example, SpO2 based on the fourth detection signal from which the noise component has been removed using the third detection signal. According to this, in addition to biological information detected and measured based on the first detection signal and the second detection signal, different biological information can be detected and measured. Accordingly, versatility of the biological sensor module 8J and thus the biological information measurement device can be enhanced.

Modifications of Embodiments

The present disclosure is not limited to the embodiments described above, and modifications, improvements, and the like made thereto in the range in which the object of the present disclosure can be exhibited are included in the present disclosure.

In each of the embodiments described above, in order to make the first light mainly light reflected by the epidermis EP, the dermis DE and the subcutaneous layer ST, and the second light mainly light reflected by the epidermis EP and the dermis DE among the first light and the second light reflected by the body of the user who is a living body, emitted from the emission position, and received by the light receiving portion, the irradiation positions of the first light and the second light with respect to the emission position are adjusted. Also, in order to adjust the irradiation position of each of the first light and the second light, the first light emitting portion is disposed such that the distance to the light reception center is within the range described above, and the second light emitting portion is disposed such that the distance to the light reception center is within the range described above.

However, the present disclosure is not limited thereto. If the distance between the irradiation position of the second light to the body of the user who is a living body and the emission position of light from the surface of the epidermis EP is a value within the range set for the distance L2, as in the biological sensor module 8F illustrated in FIG. 14, the distance between the light emission center of the second light emitting portion and the light reception center of the light receiving portion does not have to be a value within the range set for the distance L2 in the direction in which the second light emitting portion and the light receiving portion are arranged in a plan view.

In each of the embodiments described above, the first light is light of a wavelength of 500 nm or more and less than 600 nm, and the second light is a light of a wavelength of 600 nm or more. However, the present disclosure is not limited thereto, and the wavelengths of the first light and the second light can be appropriately changed according to the type of biological information to be detected. For example, at least a portion of the wavelength range of the first light and the wavelength range of the second light may be coincident as long as the first light and the second light can be distinguished according to a reflection part on the user's body.

In each of the embodiments described above, the light emission center of the first light emitting portion coincides with the center of the first light emitting portion in a plan view, and the light emission center of the second light emitting portion coincides with the center of the second light emitting portion in a plan view. However, the present disclosure is not limited thereto, and depending on the configuration of the first light emitting portion and the second light emitting portion, the light emission center may not necessarily coincide with the center of the light emitting portion in a plan view. The distance between the first light emitting portion and the light receiving portion and the distance between the second light emitting portion and the light receiving portion may not necessarily be the center-to-center distance. In addition, the centers of the first light emitting portion and the second light emitting portion may not be light emission centers, and the centers of the light receiving portions may not be light reception centers.

In each of the embodiments described above, the first region on the second light emitting portion side has a larger area in a plan view than the second region, in the light receiving portion. However, the present disclosure is not limited thereto. If the light receiving portion can receive the second light emitted from the second light emitting portion and reflected by the user's body, the area of the first region in a plan view may not be larger than the area of the second region in a plan view.

In the direction in which the second light emitting portion and the light receiving portion are arranged, the distance between the end on the light receiving portion side in the second light emitting portion and the end on the second light emitting portion side in the light receiving portion is not also limited to a value within the range described above, and may be changed as appropriate.

In each of the embodiments described above, the first light emitting portion and the second light emitting portion include light emitting elements such as an LED and an organic EL element, and the light receiving portion includes a photodiode. However, the present disclosure is not limited thereto, and the first light emitting portion, the second light emitting portion, and the light receiving portion may have any configuration as long as their respective functions can be realized.

In each of the embodiments described above, the measurement unit 4 includes the acceleration sensor 41 that detects acceleration acting on the biological information measurement device, in addition to the biological sensor modules 8A to 8J. However, the present disclosure is not limited thereto, and the acceleration sensor 41 may be omitted. In addition, the biological information measurement device may include another sensor such as a position sensor (for example, a GPS receiver) capable of measuring position information.

In each of the embodiments described above, the biological sensor modules 8A to 8H detect the pulse wave which is one of the biological information, and the processing unit 7 determines the pulse rate, which is another one of the biological information, based on the detection signal output from the biological sensor modules 8A to 8H. That is, the biological information measurement device described above measures the pulse wave and the pulse rate as biological information. Further, the biological information measurement device including the biological sensor module 8J can measure SpO2 in addition to the pulse wave and the pulse rate. However, the present disclosure is not limited thereto, and biological information that can be detected and measured by the biological information measurement device of the present disclosure is not limited to the pulse wave, the pulse rate and the SpO2. For example, the present disclosure may be applied to a biological information measurement device that measures various biological information such as heart rate variability (HRV), R-R Interval (RRI: pulse interval), blood pressure, blood sugar level, activity amount and calorie consumption, and maximum oxygen intake (VO2max).

In each of the embodiments described above, an example in which each of the biological sensor modules 8A to 8J is applied to the biological information measurement device worn on the wrist of the user is described. However, the present disclosure is not limited thereto, and the worn part on which the biological information measurement device is worn may be another part as long as the worn part is the user's upper arm, upper arm including forearm, thigh, lower leg including lower thigh, trunk, neck, ankle, and the like, where the skin is displaced by the movement of a tendon or a muscle.

What is claimed is:

1. A biological information measurement device comprising:
    a first light emitting portion that emits first light;
    a second light emitting portion that emits second light;
    a light receiving portion that receives the first light reflected by an epidermis of a skin, a dermis of the skin, and a subcutaneous layer, and the second light reflected by the epidermis and dermis of the skin;
    a light shielding portion disposed between the second light emitting portion and the light receiving portion, the light shielding portion configured to shield light emitted directly from the first light emitting portion to the light receiving portion and light emitted directly from the second light emitting portion to the light receiving portion to suppress the first light and the second light from being directly incident on the light receiving portion without passing through a body of a user; and
    a processing unit that calculates biological information by removing noise from a first detection signal output based on the first light received by the light receiving portion, using a second detection signal output based on the second light received by the light receiving portion,
    wherein a virtual line passing through a light emission center of the second light emitting portion in a direction orthogonal to a direction from the second light emitting portion toward the light receiving portion defines a virtual line VL1, and a virtual line passing through the light receiving portion that is parallel to and separated by 2 mm from the virtual line VL1 is defined as virtual line VL2, and
    a region defined by an area of the light receiving portion on a second light emitting portion side of the virtual line VL2 is larger than a remaining region of the light receiving portion in plan view.

2. The biological information measurement device according to claim 1, wherein the first light emitting portion and the second light emitting portion are disposed at positions where a path of the second light in a body of a user is included in a path of the first light in the body of the user.

3. The biological information measurement device according to claim 2, wherein a wavelength of the first light is 500 nm or more and less than 600 nm, and
    a wavelength of the second light is 600 nm or more.

4. The biological information measurement device according to claim 2, wherein a distance between the second light emitting portion and the light receiving portion is less than 2.0 mm.

5. The biological information measurement device according to claim 1, wherein a wavelength of the first light is 500 nm or more and less than 600 nm, and
a wavelength of the second light is 600 nm or more.

6. The biological information measurement device according to claim 5, wherein a distance between the second light emitting portion and the light receiving portion is less than 2.0 mm.

7. The biological information measurement device according to claim 1, wherein a distance between the second light emitting portion and the light receiving portion is less than 2.0 mm.

8. The biological information measurement device according to claim 1, wherein the second light emitting portion is disposed between the first light emitting portion and the light receiving portion in a length direction of the biological information measurement device, and
a light emission center of the second light emitting portion, a light emission center of the first light emitting portion, and a light reception center of the light receiving portion are positioned on a virtual line parallel to a length direction of the biological information measurement device.

9. The biological information measurement device according to claim 1, wherein the light shielding portion has a plate or frame shape.

10. The biological information measurement device according to claim 1, wherein the first light and the second light are received in a center of the light receiving portion in plan view.

11. A biological information measurement device comprising:
a first light emitting portion that emits first light;
a second light emitting portion that emits second light;
a light receiving portion that receives light from the first light emitting portion and the second light emitting portion and outputs a first detection signal and a second detection signal;
a light shielding portion disposed between the second light emitting portion and the light receiving portion, the light shielding portion configured to shield light emitted directly from the first light emitting portion to the light receiving portion and light emitted directly from the second light emitting portion to the light receiving portion to suppress the first light and the second light from being directly incident on the light receiving portion without passing through a body of a user; and
a processing unit that determines biological information based on the first detection signal and the second detection signal, wherein a distance between the second light emitting portion and the light receiving portion is less than 2.0 mm,
wherein a virtual line passing through a light emission center of the second light emitting portion in a direction orthogonal to a direction from the second light emitting portion toward the light receiving portion defines a virtual line VL1, and a virtual line passing through the light receiving portion that is parallel to and separated by 2 mm from the virtual line VL1 is defined as virtual line VL2, and
a region defined by an area of the light receiving portion on a second light emitting portion side of the virtual line VL2 is larger than a remaining region of the light receiving portion in plan view.

12. The biological information measurement device according to claim 11, wherein the distance between the second light emitting portion and the light receiving portion is a distance between the light emission center of the second light emitting portion and a light reception center of the light receiving portion.

13. The biological information measurement device according to claim 12, wherein the light emission center of the second light emitting portion is a center of the second light emitting portion in plan view, and
the light reception center of the light receiving portion is a center of a light receiving surface of the light receiving portion in plan view.

14. The biological information measurement device according to claim 11, wherein a wavelength of the first light is 500 nm or more and less than 600 nm, and
a wavelength of the second light is 600 nm or more.

15. The biological information measurement device according to claim 11, wherein a distance between the first light emitting portion and the light receiving portion in a direction from the first light emitting portion toward the light receiving portion is equal to or greater than a distance between the second light emitting portion and the light receiving portion in the direction from the second light emitting portion toward the light receiving portion.

16. The biological information measurement device according to claim 11, wherein a distance between the second light emitting portion and the light receiving portion in the direction from the second light emitting portion toward the light receiving portion is 0.5 mm or more and less than 2.0 mm.

17. The biological information measurement device according to claim 11, wherein the second light emitting portion is disposed between the first light emitting portion and the light receiving portion.

18. The biological information measurement device according to claim 17, wherein the second light emitting portion includes a plurality of second light emitting element groups, and the light receiving portion is provided between the plurality of second light emitting element groups, and
the first light emitting portion includes a plurality of first light emitting element groups, and the plurality of second light emitting element groups and the light receiving portion are provided between the first light emitting element groups.

19. The biological information measurement device according to claim 11, wherein the second light emitting portion is disposed between the first light emitting portion and the light receiving portion in a length direction of the biological information measurement device, and
a light emission center of the second light emitting portion, a light emission center of the first light emitting portion, and a light reception center of the light receiving portion are positioned on a virtual line parallel to a length direction of the biological information measurement device.

20. The biological information measurement device according to claim 11, wherein the light shielding portion has a plate or frame shape.

* * * * *